US010535471B2

(12) United States Patent
Millman et al.

(10) Patent No.: US 10,535,471 B2
(45) Date of Patent: Jan. 14, 2020

(54) ELECTROLYTIC CAPACITOR CONTAINING A VALVE METAL SOURCED FROM A CONFLICT-FREE MINE SITE AND A METHOD OF FORMING THEREOF

(71) Applicant: AVX Corporation, Fountain Inn, SC (US)

(72) Inventors: William A. Millman, Paignton (GB); Jan Loun, Prague (CZ)

(73) Assignee: AVX Corporation, Fountain Inn, SC (US)

( * ) Notice: Subject to any disclaimer, the term of this patent is extended or adjusted under 35 U.S.C. 154(b) by 0 days.

(21) Appl. No.: 15/710,903

(22) Filed: Sep. 21, 2017

(65) Prior Publication Data

US 2018/0082794 A1  Mar. 22, 2018

Related U.S. Application Data

(60) Provisional application No. 62/397,975, filed on Sep. 22, 2016.

(51) Int. Cl.
*H01G 9/042* (2006.01)
*H01G 9/048* (2006.01)
(Continued)

(52) U.S. Cl.
CPC ........... *H01G 9/042* (2013.01); *H01G 9/0029* (2013.01); *H01G 9/0032* (2013.01);
(Continued)

(58) Field of Classification Search
CPC .......... H01G 9/042; H01G 9/048; H01G 9/07; H01G 9/145; H01G 9/15; H01G 9/0029; H01G 9/0525; H01G 9/052
(Continued)

(56) References Cited

U.S. PATENT DOCUMENTS 5,369,547 A  11/1994 Evans
5,457,862 A  10/1995 Sakata et al.
(Continued)

FOREIGN PATENT DOCUMENTS

CN       104700097 A   6/2015
WO   WO 2010/063570 A1  6/2010
(Continued)

OTHER PUBLICATIONS

Schütte et al., "The Analytical Fingerprint (AFP) Method and Application Process Manual", Version 1.3, Hannover/Bujumbura, Jan. 2013, 47 pages.
(Continued)

*Primary Examiner* — Eric W Thomas
*Assistant Examiner* — Arun Ramaswamy
(74) *Attorney, Agent, or Firm* — Dority & Manning, P.A.

(57) ABSTRACT

A method of forming an electrolytic capacitor is provided. The method includes obtaining an unverified mineral sample from a mine site, analyzing the unverified mineral sample via quantitative mineralogical analysis and comparing data collected during the quantitative mineralogical analysis for the unverified mineral sample to data in a database that corresponds to quantitative mineralogical analysis collected for verified mineral samples sourced from one or more mine sites from a conflict-free geographic region to determine if the unverified mineral sample is sourced from one or more mine sites from the conflict-free geographic region. If it is determined that the unverified mineral sample is sourced from one or more mine sites from the conflict-free geographic region, the method then involves converting the unverified mineral sample into an anode for the electrolytic capacitor. The electrolytic capacitor can be a solid electrolytic capacitor or a wet electrolytic capacitor.

17 Claims, 14 Drawing Sheets

(51) Int. Cl.
  *H01G 9/07* (2006.01)
  *H01G 9/145* (2006.01)
  *H01G 9/00* (2006.01)
  *H01G 9/052* (2006.01)
  *H01G 9/15* (2006.01)
  *H01G 9/025* (2006.01)
  *H01G 9/035* (2006.01)

(52) U.S. Cl.
  CPC .......... *H01G 9/0036* (2013.01); *H01G 9/048* (2013.01); *H01G 9/07* (2013.01); *H01G 9/145* (2013.01); *H01G 9/15* (2013.01); *H01G 9/025* (2013.01); *H01G 9/035* (2013.01)

(58) Field of Classification Search
  USPC ............. 361/523, 528, 529; 702/2; 29/25.03
  See application file for complete search history.

(56) References Cited

U.S. PATENT DOCUMENTS

| | | | |
|---|---|---|---|
| 5,473,503 | A | 12/1995 | Sakata et al. |
| 5,729,428 | A | 3/1998 | Sakata et al. |
| 5,812,367 | A | 9/1998 | Kudoh et al. |
| 6,197,252 | B1 | 3/2001 | Bishop et al. |
| 6,322,912 | B1 | 11/2001 | Fife |
| 6,391,275 | B1 | 5/2002 | Fife |
| 6,416,730 | B1 | 7/2002 | Fife |
| 6,527,937 | B2 | 3/2003 | Fife |
| 6,576,099 | B2 | 6/2003 | Kimmel et al. |
| 6,592,740 | B2 | 7/2003 | Fife |
| 6,594,140 | B1 | 7/2003 | Evans et al. |
| 6,639,787 | B2 | 10/2003 | Kimmel et al. |
| 6,674,635 | B1 | 1/2004 | Fife et al. |
| 6,987,663 | B2 | 1/2006 | Merker et al. |
| 7,220,397 | B2 | 5/2007 | Kimmel et al. |
| 2005/0013765 | A1 | 1/2005 | Thomas et al. |
| 2005/0019581 | A1 | 1/2005 | Schnitter |
| 2005/0103638 | A1 | 5/2005 | Schnitter et al. |
| 2006/0038304 | A1 | 2/2006 | Osako et al. |
| 2008/0232037 | A1 | 9/2008 | Biler |
| 2009/0128997 | A1 | 5/2009 | Kikuchi et al. |
| 2013/0242464 | A1* | 9/2013 | Biler ................. C25D 9/02 361/504 |
| 2013/0321792 | A1 | 12/2013 | Shapiro |
| 2014/0117229 | A1 | 5/2014 | Owen |
| 2014/0304030 | A1 | 10/2014 | Bryan |
| 2014/0324347 | A1 | 10/2014 | Mazurkiewicz et al. |

FOREIGN PATENT DOCUMENTS

| | | |
|---|---|---|
| WO | WO 2016/205894 A1 | 12/2016 |
| WO | WO 2018/057682 A1 | 3/2018 |

OTHER PUBLICATIONS

Melcher, F. et al., Tantalum-(niobium-tin) mineralisation in African pegmatites and rare metal granites: Constraints from Ta—Nb oxide mineralogy, geochemistry and U—Pb geochronoloay, OreGeol Rev. (2013), http://dx.doi.org/10.1016/j.oregeorev.2013.09.003, 53 pages.

Melcher et al., "Fingerprinting of conflict minerals: columbite-tantaiite ("coitan") ores", SGA News, No. 23, Hannover, Germany, Jun. 2008; 11 pages.

Martin J. Bauwens, "Conflict Minerals Traceability Models in light of Dodd-Frank Section 1502," MJB Consulting, African Business & Legal Intelligence, May 30, 2011, 17 pages.

Matthew W. Paul, "Geology, Geochemistry and Mineralogy of Epithermal gold ores, Moonlight Prospect," Honors thesis, The University of Adelaide School of Earth and Environmental Sciences, Pajingo, North Queensland, 2010, 3 pages.

International Search Report and Written Opinion for PCT/US2017/052620, dated Jan. 9, 2018, 16 pages.

* cited by examiner

ELECTROLYTIC CAPACITOR CONTAINING A VALVE METAL SOURCED FROM A CONFLICT-FREE MINE SITE AND A METHOD OF FORMING THEREOF

CROSS REFERENCE TO RELATED APPLICATIONS

The present application claims the benefit of U.S. Provisional Application Ser. No. 62/397,975 having a filing date of Sep. 22, 2016, which is incorporated herein by reference for all purposes.

BACKGROUND OF THE INVENTION

Conflict resources are natural resources (i.e., resources that exist without the actions of humankind) that are found in geographic regions termed "conflict zones" and are often sold to finance armed conflict and civil wars. An example of a conflict resource is a conflict mineral. The most common conflict minerals include columbite-tantalite (i.e., coltan), cassiterite, wolframite, and gold. Coltan is the metal ore from which the elements tantalum and niobium are extracted, cassiterite is the main ore needed to produce tin, and wolframite is a source of the element tungsten. Another conflict mineral is microlite, which is another ore from which tantalum is extracted. One particular region in which conflict minerals have been mined and sold in order to perpetuate conflict is the Democratic Republic of Congo (DRC).

The Dodd-Frank Wall Street Reform and Consumer Protection Act was signed into law in the United States in 2010 and requires U.S. and certain foreign companies to report and make public their use of conflict minerals from the DRC and its surrounding countries (e.g., Angola, Burundi, Central African Republic, Congo Republic, Rwanda, Sudan, Tanzania, Uganda, and Zambia) in their products. A similar law has been passed in Europe, but it extends to all countries rather than just the DRC and adjoining countries. The U.S. Conflicts Minerals Law requires independent third party supply chain traceability audits and reporting of audit results to the public and the Securities and Exchange Commission. In order to comply with the auditing and reporting requirements and ensure that companies are not using conflict minerals in their products, an accurate, reliable method for identifying the geographic origin of a mineral (e.g., the mine site or mine sites from which it is sourced) to ensure that it is a conflict-free mineral would be useful as first step in the processes involved in making various products that include materials prevalent in geographic regions of conflict.

Because many electrolytic capacitors include valve metals, where there is a risk that such valve metals have been sourced from geographic regions where conflict is present, a need exists for an electrolytic capacitor and a method of making thereof, where it can be verified that the valve metal is sourced from a conflict-free mine site.

SUMMARY OF THE INVENTION

In accordance with one embodiment of the present invention, a method of forming an electrolytic capacitor is disclosed that comprises obtaining an unverified mineral sample from a mine site and analyzing the unverified mineral sample via quantitative mineralogical analysis and comparing data collected during the quantitative mineralogical analysis for the unverified mineral sample to data in a database that corresponds to quantitative mineralogical analysis collected for verified mineral samples sourced from one or more mine sites from a conflict-free geographic region to determine if the unverified mineral sample is sourced from the one or more of the mines sites from the conflict-free geographic region. Further, if it is determined that the unverified mineral sample is sourced from the one or more of the mine sites from the conflict-free geographic region, the unverified mineral sample is then converted into an anode for the electrolytic capacitor.

In accordance with another embodiment of the present invention, a solid electrolytic capacitor is disclosed that comprises an anode and a solid electrolyte overlying the anode. The anode includes an anodically oxidized pellet formed from a pressed and sintered valve metal powder. Further, it is verified that the valve metal powder is sourced from one or more mine sites from a conflict-free geographic region by analyzing an unverified mineral sample from which the valve metal powder is obtained via quantitative mineralogical analysis and comparing data collected during the quantitative mineralogical analysis for the unverified mineral sample to data in a database that corresponds to quantitative mineralogical analysis collected for verified mineral samples sourced from the one or more mine sites from the conflict-free geographic region to determine that the unverified mineral sample is sourced from the one or more mine sites from the conflict-free geographic region.

In accordance with yet another embodiment of the present invention, a wet electrolytic capacitor is disclosed that comprises an anode, a cathode that comprises a metal substrate coated with a conductive coating, and a fluidic working electrolyte in communication with the anode body and the cathode. The anode includes an anodically oxidized pellet formed from a pressed and sintered valve metal powder. Further, it is verified that the valve metal powder is sourced from one or more mine sites from a conflict-free geographic region by analyzing an unverified mineral sample from which the valve metal powder is obtained via quantitative mineralogical analysis and comparing data collected during the quantitative mineralogical analysis for the unverified mineral sample to data in a database that corresponds to quantitative mineralogical analysis collected for verified mineral samples sourced from the one or more mine sites from a conflict-free geographic region to determine that the unverified mineral sample is sourced from the one or more mine sites from a conflict-free geographic region.

Other features and aspects of the present invention are described in more detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
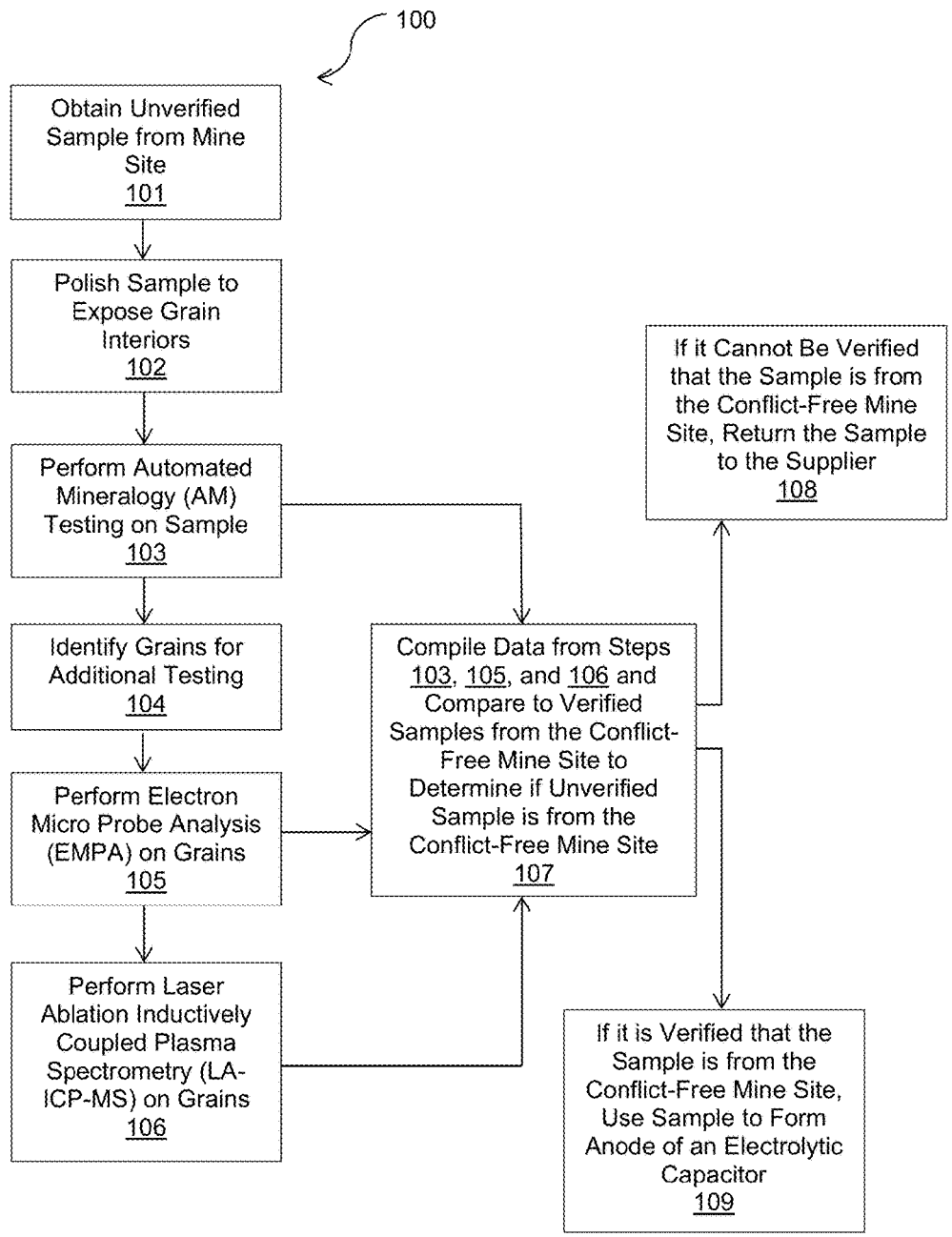
FIG. 1 is a block diagram illustrating a method for determining the geographic origin of a mineral sample.

Repeat use of reference characters in the present specification and drawings is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to an electrolytic capacitor (e.g., a solid electrolytic capacitor or a wet electrolytic capacitor) containing a valve metal sourced from a conflict-free mine site and a method of forming thereof. The method includes obtaining an unverified mineral sample (e.g., an ore concentrate that has not yet been smelted to a pure metal or tantalum oxide) from a mine site and analyzing the unverified mineral sample via quantitative mineralogical analysis and comparing data collected during the quantitative mineralogical analysis for the unverified mineral sample to data in a database that corresponds to quantitative mineralogical analysis collected for verified mineral samples sourced from one or more mine sites from a conflict-free geographic region to determine if the unverified mineral sample is sourced from the one or more mine sites from the conflict-free geographic region. Analyzing the unverified mineral sample can include performing automated mineralogy testing on the sample, identifying grains for further testing, and performing electron microprobe analysis and laser ablation inductively coupled plasma spectrometry on the identified grains. If it is determined that the unverified mineral sample is sourced from one or more of the mines sites from the conflict-free geographic region, the method then involves converting the unverified mineral sample into an anode for the electrolytic capacitor.

It should be understood that the mineral determination methods described herein are based on the fact that geological units, geographic regions, and even specific mine sites within a geographic region are distinguished from each other due to their distinct geological characteristics. For example, the regional and local variations in the composition of tantalum minerals reflect the conditions of formation, the geological environment (e.g., host rocks), and the age of the emplacement of the host pegmatite. These factors influence the presence specific minerals, as well as their basic and detailed characteristics, the enrichment of major and minor elements, and the presence or absence of other mineralogical and geochemical features. Tantalum ores, for instance, are in most cases represented by the columbite-tantalite group minerals and to a lesser extent by other minerals (e.g., microlite, wodginite, tapiolite, etc.). The most abundant tantalum minerals at a specific mine site should be analyzed via the steps outlined in the method of the present invention, while additional minerals can be added to any or all of the steps if there is a need to increase the level of confidence regarding the origin of the mineral sample or concentrate.

Specifically, prior to using the valve metal to form the anode component of the electrolytic capacitor, the present inventors have developed a methodology for determining whether or not the alleged conflict-free valve metal (for instance, a valve metal that has been independently validated and alleged to by conflict-free via a mineral determination method) received from a supplier is in fact sourced from a conflict-free mine site. It is also to be understood that this methodology can be used to compare samples for risk mitigation purposes in order to determine if a sample received from a supplier is sourced from a mine site located in a geographic region that has been approved by the capacitor manufacturer, where such information can be used for investigative purposes if an outlier sample (a sample that cannot be matched with any of the approved or verified samples in the database) is received. A general description of the method is shown in FIG. 1.

Turning to FIG. 1, the method 100 of forming an electrolytic capacitor from a conflict-free valve metal powder includes first obtaining an unverified sample (i.e., a sample that has not been verified as conflict-free) from a mine site, where the sample may have been independently validated or described as conflict-free by another party (step 101). The sample can be self-collected as a heavy-mineral panned concentrate directly at the mine site to be sure about the origin of the sample and to collect the sample before any further processing is carried out to preserve the complete heavy mineral association. Next, in step 102, a section of the sample is formed to a polished epoxy section having a diameter of about 25 millimeters (mm), which is then coated with a carbon layer having a thickness of about 10 nanometers (nm) to prepare the sample for testing.

Then, in step 103, the polished section is scanned via automated mineralogy (AM) to determine the specific minerals present in the sample as well as the prevalence and distribution of each of the minerals in the polished section, where samples taken from the same mine site and depth should include the same minerals and at substantially the same prevalence and distribution. If samples from the same mine site and depth do not include substantially the same minerals with substantially the same prevalence and distribution, then it is possible that the supplier added extraneous material to the sample before shipment. Thereafter, in step 104, grains from the polished section of the sample are selected for further analysis. For example, 50 grains containing tantalum, as determined from the AM scan, are selected for further analysis.

Next, in step 105, electron micro probe analysis (EMPA) is carried out on the selected grains. The raw EMPA data provides for the major and minor elements of the 50 grains based on weight percentage (see Table 1 below). The major elements for columbite-tantalite group (CGM) minerals can include tantalum (Ta), niobium (Nb), iron (Fe), and manganese (Mn), while the major elements for microlite can include tantalum (Ta), calcium (Ca), Sodium (Na), and fluorine (F). The minor/trace elements for CGM minerals can include titanium (Ti), tin (Sn), tungsten (W), scandium (Sc), zirconium (Zr), hafnium (Hf), uranium (U), thorium (Th), bismuth (Bi), antimony (Sb), yttrium (Y), lithium (Li), lead (Pb), magnesium (Mg), rare earth elements (REE) (e.g., lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), etc. The minor/trace elements for microlite can include niobium (Nb), titanium (Ti), uranium (U), thorium (Th), tin (Sn), lead (Pb), bismuth (Bi), barium (Ba), antimony (Sb), iron (Fe), manganese (Mn), tungsten (W), scandium (Sc), zirconium (Zr), yttrium (Y), lithium (Li), magnesium (Mg), rare earth elements (REE) (e.g., lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), etc.

Further, in step 106, laser ablation inductively coupled plasma spectrometry (LA-ICP-MS) is performed on selected grains to determine the trace/minor elements and rare earth elements present in the grains in parts per million (ppm).

In step 107, data from steps 103, 104, and 106 is then compiled to determine if the characteristics of the unverified sample from the allegedly conflict-free mine site substantially match the characteristics of verified samples from one or more conflict-free mine sites. If so, it can be assumed that the unverified sample in fact originated and was sourced from a validated conflict-free mine site so that the now verified sample can be used to form the electrolytic capacitor of the present invention.

Details regarding the various steps are described in more detail below.

I. Determining if a Valve Metal Sample Originates from a Conflict-Free Mine Site A. Sample Receipt (101) and Preparation (102)

First, a mineral sample is obtained from a mine site, where the mineral sample is a mineral pre-concentrate (raw ore) or concentrate (raw ore that is finely ground and from which waste has been removed). The mineral sample can weigh between about 25 grams and about 125 grams, such as from about 50 grams to about 100 grams, in order to obtain a representative sample of the mineral. The mineral sample is then reduced to a smaller sample that can weigh between about 2.5 grams and about 12.5 grams, such as between about 5 grams and about 10 grams. The grains in the smaller sample are then formed into a polished epoxy section on a sample mount having a diameter of about 25 millimeters (mm) so that the grain interiors are exposed for subsequent analysis, after which the polished epoxy section is coated with a carbon layer having a thickness of about 10 nanometers (nm).

B. Automated Mineralogy Analysis Using Scanning Electron Microscopy and Energy Dispersive Spectroscopy (103)

Next, after a sample has been mounted and polished as discussed above, the sample is analyzed quantitatively via automated mineralogy (AM) to determine its mineralogical composition via quantitative analysis. The mounted sample is analyzed using a scanning electron microscopy (SEM)-based mineral analyzer combined with an energy dispersive spectrometer (EDS). Such a device provides information on the proportions of minerals in the polished section, which are then chemically characterized using EDS without a need to move the sample or perform a new search for specific particles. The result is (1) an AM image that distinguished the various minerals in the sample by color/shading and (2) information on the proportional presence of the various minerals in a pie chart or bar chart. The AM image provides valuable textural and mineralogical information (e.g., liberation degree, mineral association, grain size, intergrowths of minerals, inclusions, etc.).

An example of a machine that performs such automated mineralogy (AM) analysis is a Tescan Integrated Mineral Analyzer (TIMA) available from TESCAN ORSAY HOLDING (Czech Republic). The TIMA a fully automated, high throughput, analytical scanning electron microscope designed specifically for the mining and minerals processing industry. The TIMA is useful for mineral liberation analysis, process optimization, remediation, and search for precious metals and rare earths. TIMA measures modal abundance, size-by-size liberation, mineral association, etc. and performs a PGM search automatically on multiple samples of grain mounts and thin or polished sections. The technology is based on a completely integrated EDX system that performs full spectrum imaging at very fast scan speeds. Image analysis in TIMA is performed simultaneously with SEM backscattered electron images and a suite of X-ray images. The level of hardware integration of the SEM and EDX allows for fully automated data collection.

Using the software, the polished surface of the mounted sample is scanned by an electron beam and the resulting back-scatter electrons are collected to generate electronic image information. All mineral grains exposed on the sample surface are then automatically analyzed using energy-dispersive X-ray spectrometry, where a characteristic X-ray spectrum is produced for each particle. This information is then compared to a calibrated standard mineral reference database. The automated mineralogy (AM) software is able to automatically identify individual minerals at a spatial resolution of 0.005 millimeters and then quantifies the percent abundance of each mineral present in the mounted sample, noting that the percent abundance of a specific mineral in sample depends on numerous variables such as the specific individual who prepared the panned sample, whether the sample was magnetically or gravity separated, etc.

As a result of AM and as mentioned above, the minerals present in the sample can be determined by viewing a color-coded or shaded scan of the polished section, and then individual grains can be selected for further detailed study and analysis in steps C and D below. In addition, AM provides information regarding grain size, liberation degree, mineral association, intergrowths of specific minerals, inclusions, etc., which may be unique depending on the geographic region from which the sample was obtained. Further, possible mixing in of a material from a different mine (e.g., adding in microlite to a columbite-tantalite ore) can be revealed via AM. In addition, it is noted that the proportion of minerals may change slightly over time between samples taken from the same mine site due to changing geology during mining, different degrees of ore processing, etc. However, if the proportion of minerals changes significantly, then the supplier or third party must give an explanation.

Figure 3:
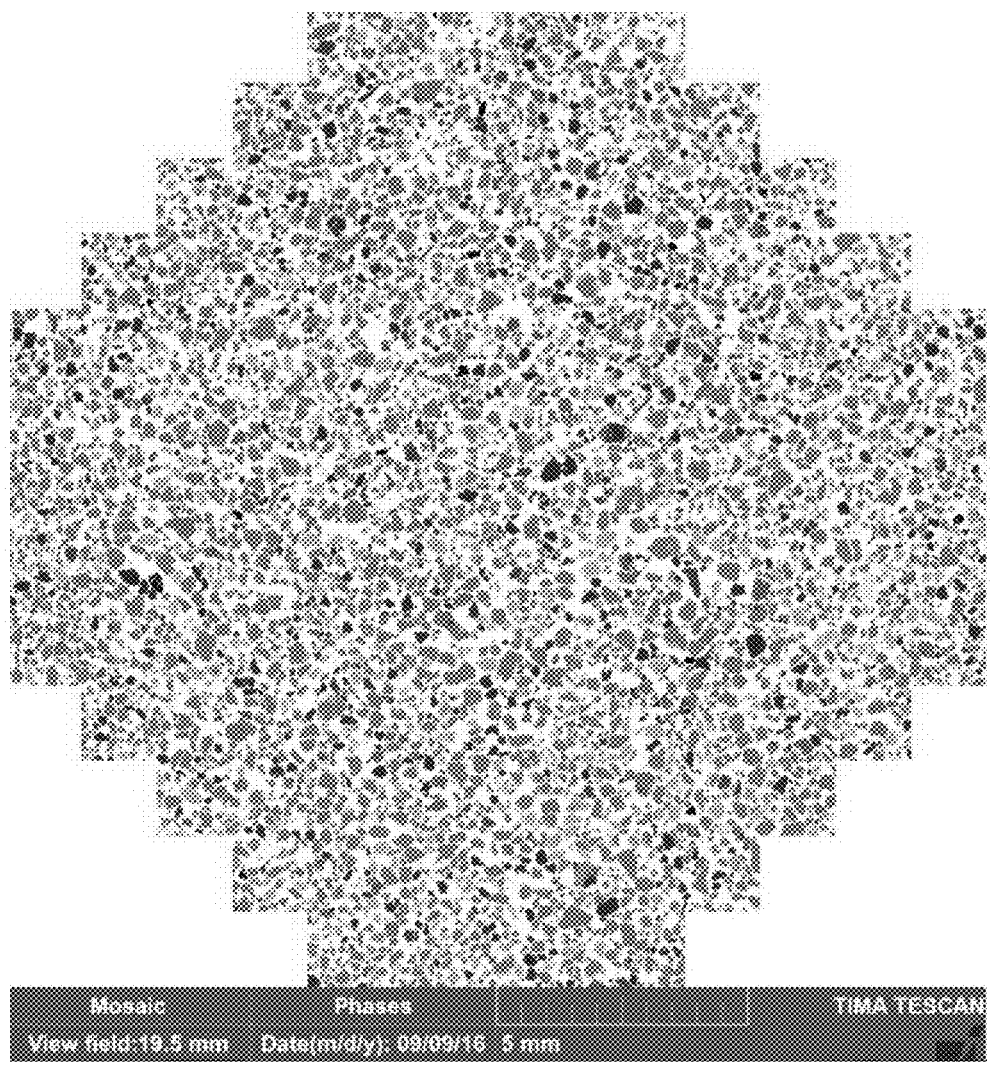
FIG. 3 is an automated mineralogy scan (using TIMA) for a polished microlite sample where various minerals in the sample are shaded by species.
Figure 4A:
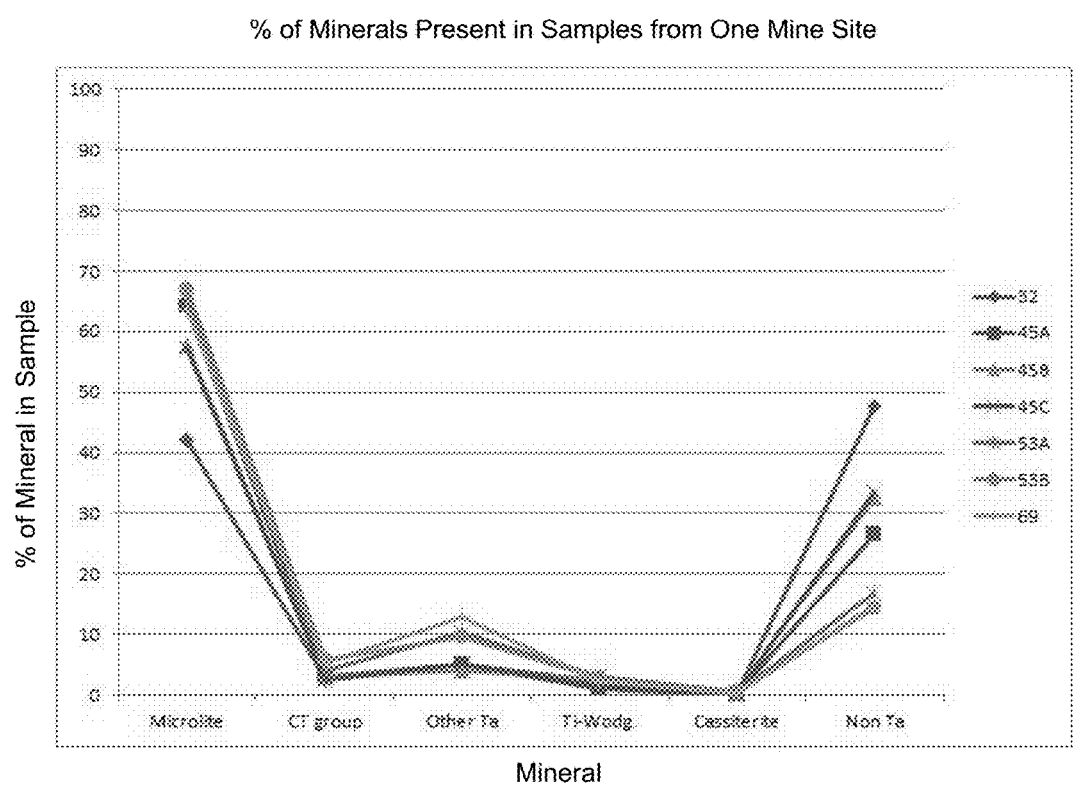
FIG. 4A is an automated mineralogy (AM) chart that shows the summarized proportions (in %) of minerals present in samples received from one mine site.
Figure 4B:
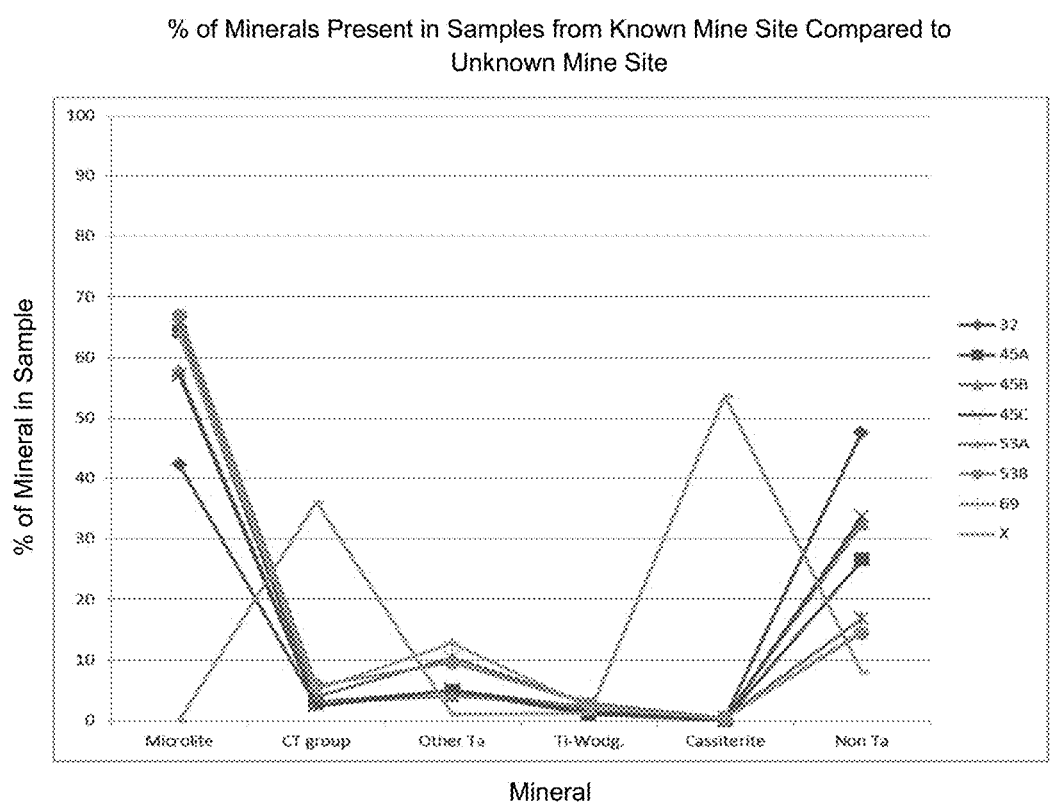
FIG. 4B is an automated mineralogy (AM) chart that shows the summarized proportions (in %) of minerals present in samples received from one mine site (samples 32, 45A, 45B, 45C, 53A, 53B, and 69) compared to a sample received from a new or unknown source (sample X)
Figure 4C:
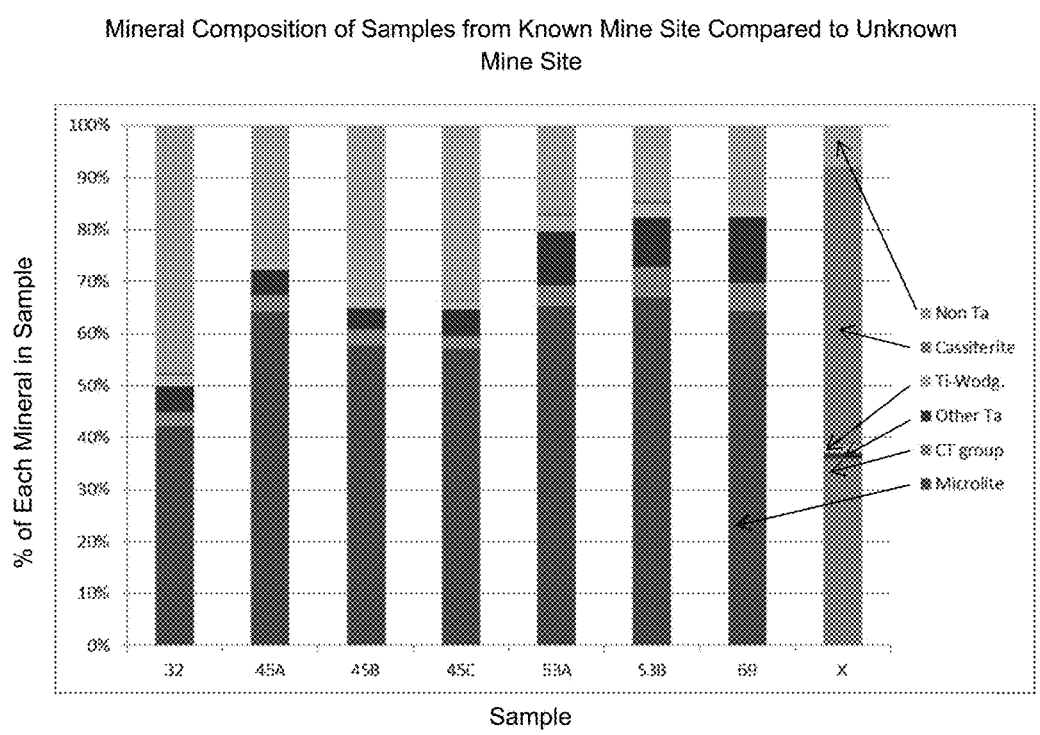
FIG. 4C is an automated mineralogy (AM) bar chart that shows the summarized proportions (in %) of minerals present in samples received from one mine site (samples 32, 45A, 45B, 45C, 53A, 53B, and 69) compared to a sample received from a new or unknown source (sample X)

FIG. 3 and Table 1, along with FIGS. 4A, 4B, and 4C, show the information that can be gathered during AM analysis of a mineral sample. Specifically, FIG. 3 is an automated mineralogy scan (using TIMA) for a polished microlite sample where various minerals in the sample are shaded by species. Meanwhile, Table 1 below shows the various minerals present in the scan of FIG. 3 in terms of mass %.

TABLE 1

Minerals Present in the TIMA Scan of FIG. 3 by Mass %
Minerals Present in Sample of FIG. 3 by Mass %

| Mineral | Mass % of Phase (%) |
|---|---|
| Microlite | 64.22 |
| Muscovite | 13.46 |
| Quartz | 6.43 |
| Al2SiO5 Polymorphs | 3.63 |
| Other Ta Phases | 2.81 |
| Uranomicrolite | 2.1 |
| Tantalite-(Fe) | 1.41 |
| Columbite | 1.38 |
| Titanowodginite | 1.14 |
| Hafnon | 0.58 |
| Schorl | 0.43 |
| Tantalite-(Mn) | 0.25 |
| Zircon | 0.21 |
| Ilmenite | 0.16 |
| Kaolinite | 0.16 |
| Hematite/Magnetite | 0.08 |
| Cassiterite | 0.06 |
| Gold | 0.04 |
| Columbite-(Mn) | 0.04 |
| Staurolite | 0.03 |
| Monazite | 0.03 |
| Anorthite | 0.03 |
| Romanechite | 0.03 |
| Orthoclase | 0.02 |
| Rutile | 0.02 |

TABLE 1-continued

Minerals Present in the TIMA Scan of FIG. 3 by Mass %
Minerals Present in Sample of FIG. 3 by Mass %

| Mineral | Mass % of Phase (%) |
|---|---|
| Florencite-(Ce) | 0.02 |
| Albite | 0.01 |
| Ferrotitanowodginite | 0.01 |
| Rutile (Fe) | 0.01 |
| Almandine Spessartine | 0.01 |
| Unclassified | 1.21 |

Further, FIG. 4A is an automated minerology (AM) chart shows the summarized proportions (in %) of minerals present in seven samples (samples 32, 45A, 45B, 45C, 53A, 53B, and 69) received from one mine site; FIG. 4B is an automated minerology (AM) chart that shows the summarized proportions (in mass %) of minerals present in samples received from one mine site (samples 32, 45A, 45B, 45C, 53A, 53B, and 69) compared to a sample received from a new or unknown source (sample X); and FIG. 4C is an automated minerology (AM) bar chart that shows the summarized proportions (in %) of minerals present in samples received from one mine site (samples 32, 45A, 45B, 45C, 53A, 53B, and 69) compared to a sample received from a new or unknown source (sample X). In FIGS. 4A through 4C, the term "microlite" refers to that amount of tantalum oxide with high tantalum levels (such as around 60% $Ta_2O_5$) present, the term "CT group" refers to the sum of columbite-tantalite group minerals present (i.e., tantalite-Mn, tantalite-Fe, columbite-Fe, and columbite-Mn), the term "other Ta" refers to the sum of other tantalum minerals present (uranmicrolite, ixiolite, ferrotitanowodginite, etc.), the term "Ti-Wodg" refers to the amount of titanowodginite (tantalum oxide with high Ta levels, such as around 60% $Ta_2O_5$) present, the term "cassiterite" refers to the amount of tin (Sn) oxide present, and the term "non-Ta" refers to the sum of other minerals free of tantalum present in sample.

C. Electron Micro Probe Analysis (104 and 105)

Next, between about 25 grains and 125 grains, such as about 50 grains to about 100 grains, such as 50 grains, selected from the AM scan of the mounted sample are analyzed using electron micro probe analysis (EMPA), which utilizes a combination of an electron microscope and an X-ray spectrometer, where X-rays are detected based on energy (EDS) and/or wavelength (WDS). The grains are randomly selected from the grains present for the specific mineral of interest, but it is to be understood that grains that have been altered or cracked are excluded from EMPA analysis. EMPA, also called electron probe microanalysis (EPMA), is an analytical technique that is used to establish the composition of small areas of samples via quantitative analysis. An example of a machine that can perform such analysis is the CAMECA SX100 Electron Microprobe, available from CAMECA (France). The microprobe can be operated at a 15 kiloVolt acceleration voltage and a 20 nanoAmp sample current with a beam size of 5 micrometers, although other suitable parameters can also be used for operating the microprobe.

EMPA is a particle-beam technique where a beam of accelerated electrons is focused on the surface of a specimen using a series of electromagnetic lenses, and these energetic electrons produce characteristic X-rays within a small volume (typically 1 to 9 cubic microns) of the sample at its surface. The characteristic X-rays are detected at particular wavelengths, and their intensities are measured to determine concentrations of elements within the sample. All elements except hydrogen (H), helium (He), and lithium (Li) can be detected because each element has a specific set of X-rays that it emits. EMPA has a high spatial resolution and sensitivity, and individual analyses are reasonably short, requiring only a minute or two in most cases. Additionally, the electron microprobe can function like a scanning electron microscope (SEM) and obtain highly magnified secondary and backscattered electron images of a sample. From EMPA, the weight percentage of the major elements and trace/minor elements or their oxides as well as evolutionary trends of the sample can be determined, as shown below in Table 2 for 60 different grains from the same sample as an example.

TABLE 2

EMPA Major and Minor Elements (Wt. %)
Weight %

| Na | Ta | Al | Y | Mg | Nb | Pb | U | Th | Si | Ti | Ca | Fe |
|---|---|---|---|---|---|---|---|---|---|---|---|---|
| 3.611 | 54.562 | 0.01 | 0 | 0.005 | 7.66 | 0 | 0.036 | 0.034 | 0.08 | 0.053 | 6.918 | 0.007 |
| 4.136 | 57.725 | 0 | 0.013 | 0 | 5.708 | 0 | 0 | 0 | 0 | 0.011 | 6.887 | 0.021 |
| 4.402 | 58.696 | 0.003 | 0.063 | 0.003 | 5.726 | 0 | 0 | 0.079 | 0 | 0 | 6.725 | 0 |
| 4.046 | 61.637 | 0.004 | 0.017 | 0 | 3.138 | 0.008 | 0.038 | 0.001 | 0 | 0.124 | 6.935 | 0 |
| 4.035 | 59.789 | 0 | 0 | 0 | 2.76 | 0.073 | 0 | 0 | 0.014 | 0.022 | 6.705 | 0 |
| 4.332 | 56.907 | 0 | 0.028 | 0 | 6.278 | 0 | 0 | 0.048 | 0 | 0.009 | 6.029 | 0 |
| 4.068 | 55.146 | 0.004 | 0.012 | 0 | 6.275 | 0.006 | 0.206 | 0.017 | 0 | 0.022 | 7.003 | 0 |
| 4.068 | 59.885 | 0 | 0.045 | 0.002 | 3.121 | 0 | 0.091 | 0 | 0 | 0 | 6.372 | 0.022 |
| 4.262 | 60.373 | 0.007 | 0 | 0 | 3.427 | 0.061 | 0 | 0.002 | 0 | 0.003 | 6.362 | 0 |
| 4.1 | 57.737 | 0.002 | 0.04 | 0 | 5.787 | 0 | 0 | 0 | 0.01 | 0.009 | 6.632 | 0 |
| 4.222 | 57.651 | 0 | 0.019 | 0.006 | 5.722 | 0 | 0 | 0.027 | 0.116 | 0.018 | 6.17 | 0 |
| 0 | 51.056 | 0.013 | 0.025 | 0 | 12.874 | 0.075 | 0 | 0.009 | 0.003 | 3.387 | 0 | 7.534 |
| 4.152 | 60.745 | 0 | 0.005 | 0.002 | 2.828 | 0.014 | 0 | 0.038 | 0.001 | 0.001 | 5.73 | 0.007 |
| 4.02 | 59.271 | 0 | 0.012 | 0 | 3.631 | 0 | 0.008 | 0.004 | 0 | 0.014 | 6.605 | 0.015 |
| 4.091 | 59.151 | 0.01 | 0.049 | 0 | 4.81 | 0 | 0 | 0.043 | 0 | 0 | 6.839 | 0 |
| 4.193 | 61.345 | 0 | 0 | 0 | 2.65 | 0 | 0 | 0 | 0.025 | 0.009 | 5.634 | 0 |
| 4.056 | 60.37 | 0.012 | 0.005 | 0 | 3.638 | 0 | 0 | 0.035 | 0 | 0.026 | 6.478 | 0 |
| 0.012 | 55.67 | 0 | 0.051 | 0.003 | 8.819 | 0 | 0 | 0 | 0 | 0 | 0 | 6.013 |
| 4.072 | 55.709 | 0 | 0.019 | 0 | 6.146 | 0.063 | 0 | 0.043 | 0 | 0.047 | 6.203 | 0.006 |
| 4.255 | 56.462 | 0 | 0.016 | 0 | 6.443 | 0 | 0.057 | 0.014 | 0 | 0.038 | 6.743 | 0.022 |
| 3.962 | 59.045 | 0.003 | 0.023 | 0.002 | 4.518 | 0.01 | 0.054 | 0 | 0.007 | 0 | 7.081 | 0 |
| 4.221 | 57.098 | 0 | 0.025 | 0.001 | 5.902 | 0 | 0.03 | 0.03 | 0.013 | 0.207 | 6.827 | 0.029 |
| 4.161 | 58.494 | 0 | 0.035 | 0.001 | 5.801 | 0 | 0.002 | 0.042 | 0 | 0.01 | 6.97 | 0.015 |
| 4.128 | 60.393 | 0.009 | 0.049 | 0 | 4.428 | 0 | 0.004 | 0 | 0.02 | 0 | 6.127 | 0 |
| 3.618 | 63.122 | 0 | 0.007 | 0 | 2.296 | 0.011 | 0.082 | 0.064 | 0.011 | 0.037 | 6.319 | 0.013 |
| 3.969 | 57.706 | 0.004 | 0 | 0.001 | 4.522 | 0.058 | 0.778 | 0.055 | 0 | 0.105 | 6.121 | 0.041 |
| 4.028 | 59.377 | 0 | 0.05 | 0 | 3.517 | 0 | 0.17 | 0.021 | 0.01 | 0.208 | 6.181 | 0.003 |
| 4.072 | 60.538 | 0.004 | 0 | 0 | 3.186 | 0 | 0.078 | 0 | 0 | 0.023 | 6.512 | 0.01 |
| 4.146 | 59.414 | 0.011 | 0.014 | 0.006 | 4.536 | 0.01 | 0 | 0.023 | 0.013 | 0 | 7.105 | 0.027 |
| 3.9 | 61.772 | 0 | 0.004 | 0 | 2.753 | 0.029 | 0 | 0 | 0 | 0.051 | 6.659 | 0 |
| 4.032 | 60.721 | 0.011 | 0.032 | 0 | 3.018 | 0 | 0.104 | 0 | 0.008 | 0.115 | 6.494 | 0 |
| 3.566 | 59.631 | 0.002 | 0.001 | 0 | 2.792 | 0.049 | 0.558 | 0.035 | 0.002 | 0.255 | 6.503 | 0 |
| 3.968 | 59.157 | 0.012 | 0.002 | 0.003 | 3.047 | 0 | 0.1 | 0 | 0.017 | 0.003 | 5.733 | 0 |
| 3.746 | 60.983 | 0 | 0.042 | 0 | 2.991 | 0 | 0.193 | 0 | 0.009 | 0.019 | 6.331 | 0.002 |
| 2.158 | 59.722 | 0 | 0 | 0.002 | 5.077 | 0.01 | 0 | 0 | 0.079 | 0.079 | 3.677 | 0.298 |
| 0 | 57.79 | 0 | 0.029 | 0.001 | 8.297 | 0.04 | 0 | 0.012 | 0 | 0.18 | 0 | 3.844 |
| 0.024 | 51.238 | 0 | 0.034 | 0.002 | 12.627 | 0 | 0 | 0.022 | 0.002 | 0.291 | 0 | 7.908 |
| 0.026 | 55.77 | 0.031 | 0 | 0.005 | 4.772 | 0.158 | 0.33 | 0 | 0.028 | 3.337 | 0 | 0 |
| 0 | 52.724 | 0.001 | 0.032 | 0 | 11.019 | 0.08 | 0.015 | 0 | 0.227 | 0.076 | 0.115 | 6.609 |
| 0.035 | 49.664 | 0.002 | 0.079 | 0.008 | 13.864 | 0 | 0 | 0.019 | 0.005 | 0.11 | 0 | 7.404 |
| 0.009 | 19.872 | 0.002 | 0.073 | 0.013 | 38.52 | 0.015 | 0.002 | 0 | 0.023 | 0.038 | 0 | 1.843 |
| 0 | 64.813 | 0 | 0.013 | 0 | 2.16 | 0 | 0.016 | 0.036 | 0 | 0.061 | 0.071 | 10.524 |
| 0.031 | 58.597 | 0.001 | 0.088 | 0.002 | 6.543 | 0 | 0.006 | 0 | 0.037 | 0.038 | 0.239 | 7.133 |
| 0 | 27.467 | 0.01 | 0.084 | 0.019 | 31.797 | 0 | 0 | 0 | 0.016 | 0.196 | 0.076 | 12.241 |
| 0.005 | 46.294 | 0 | 0 | 0 | 12.569 | 0 | 0 | 0 | 0.019 | 0.01 | 0.075 | 5.197 |
| 0 | 20.627 | 0.011 | 0.099 | 0.09 | 36.267 | 0 | 0 | 0 | 0.265 | 0.748 | 0 | 12.927 |
| 2.796 | 54.793 | 0.009 | 0 | 0.004 | 7.52 | 0.021 | 0.034 | 0.092 | 0.015 | 0.249 | 5.504 | 2.383 |
| 0.01 | 56.793 | 0.012 | 0.06 | 0 | 8.153 | 0 | 0 | 0 | 0.016 | 0.041 | 0 | 6.192 |
| 0 | 49.624 | 0.026 | 0.024 | 0 | 9.196 | 0.037 | 0.003 | 0.027 | 0.06 | 0.044 | 0 | 0.409 |
| 0.23 | 64.137 | 0.024 | 0 | 0 | 2.514 | 0 | 0.006 | 0 | 0.008 | 0.138 | 0.71 | 0.015 |
| 4.077 | 60.173 | 0.013 | 0 | 0 | 3.122 | 0 | 0 | 0 | 0.005 | 0 | 5.73 | 0 |
| 4.176 | 57.794 | 0.013 | 0.054 | 0 | 5.168 | 0.034 | 0 | 0.051 | 0 | 0.014 | 6.384 | 0 |
| 3.973 | 55.974 | 0.004 | 0 | 0 | 6.091 | 0 | 0.369 | 0.055 | 0.008 | 0.019 | 6.524 | 0 |
| 4.268 | 61.733 | 0.005 | 0.016 | 0.002 | 2.962 | 0 | 0 | 0 | 0 | 0 | 6.305 | 0 |
| 3.966 | 57.862 | 0.001 | 0.007 | 0 | 4.521 | 0 | 0 | 0.052 | 0.018 | 0.029 | 6.332 | 0 |
| 0.007 | 23.946 | 0.003 | 0.088 | 0.001 | 35.085 | 0.014 | 0 | 0 | 0.075 | 0.126 | 0 | 7.697 |
| 4.221 | 57.698 | 0.012 | 0 | 0.005 | 6.044 | 0 | 0.01 | 0 | 0.001 | 0 | 7.12 | 0.035 |
| 3.983 | 55.608 | 0 | 0.007 | 0 | 5.742 | 0 | 0.018 | 0.02 | 0 | 0.035 | 6.333 | 0.024 |
| 0.716 | 53.067 | 0.03 | 0.005 | 0.008 | 5.813 | 0.032 | 0 | 0.01 | 0.115 | 0.145 | 2.201 | 0.005 |
| 4.094 | 55.311 | 0.023 | 0.026 | 0.011 | 6.021 | 0 | 0 | 0.057 | 0.05 | 0.006 | 0.035 | 6.344 | 0.03 |

| Mn | W | Zn | Zr | Sn | Bi | Sb | Sc | F | O | Total |
|---|---|---|---|---|---|---|---|---|---|---|
| 0.008 | 0 | 0 | 0 | 0.391 | 0.028 | 0.074 | 0.011 | 3.698 | 19.66 | 96.847 |
| 0.015 | 0 | 0 | 0 | 0.773 | 0 | 0.104 | 0.008 | 4.038 | 19.661 | 99.101 |

TABLE 2-continued

EMPA Major and Minor Elements (Wt. %)
Weight %

| | | | | | | | | | | |
|---|---|---|---|---|---|---|---|---|---|---|
| 0 | 0.014 | 0 | 0.033 | 0.216 | 0.017 | 0.003 | 0 | 4.089 | 19.765 | 99.831 |
| 0.024 | 0 | 0 | 0.059 | 0.64 | 0.028 | 0 | 0 | 3.977 | 19.453 | 100.128 |
| 0.004 | 0 | 0 | 0.024 | 0.675 | 0 | 0 | 0.006 | 3.944 | 18.717 | 96.767 |
| 0.006 | 0.067 | 0 | 0.052 | 0.144 | 0.175 | 0.077 | 0.007 | 4.022 | 19.332 | 97.512 |
| 0.004 | 0 | 0.01 | 0 | 1.026 | 0 | 0 | 0.028 | 3.99 | 19.45 | 97.266 |
| 0.006 | 0 | 0 | 0.017 | 0.843 | 0.056 | 0.035 | 0.008 | 3.989 | 18.826 | 97.386 |
| 0.004 | 0 | 0 | 0.036 | 0.513 | 0.034 | 0 | 0 | 3.941 | 19.013 | 98.038 |
| 0.023 | 0 | 0 | 0.025 | 0.247 | 0.034 | 0 | 0.002 | 4.093 | 19.446 | 98.188 |
| 0.026 | 0 | 0 | 0.083 | 0.274 | 0.073 | 0.173 | 0 | 4.017 | 19.45 | 98.047 |
| 5.004 | 0.066 | 0 | 0.003 | 0.158 | 0 | 0.036 | 0.093 | 0.265 | 20.85 | 98.453 |
| 0 | 0 | 0.038 | 0.018 | 0.365 | 0 | 0 | 0.056 | 3.952 | 18.534 | 96.484 |
| 0 | 0 | 0 | 0 | 0.842 | 0 | 0.034 | 0.016 | 4.016 | 18.962 | 97.45 |
| 0 | 0 | 0 | 0.059 | 0.452 | 0 | 0.004 | 0 | 4.029 | 19.472 | 99.008 |
| 0.004 | 0 | 0.02 | 0.057 | 0.246 | 0 | 0 | 0 | 3.856 | 18.536 | 96.574 |
| 0.009 | 0 | 0 | 0.01 | 0.251 | 0 | 0 | 0.002 | 3.988 | 19.018 | 97.899 |
| 5.857 | 0 | 0.012 | 0.059 | 0.014 | 0 | 0 | 0.015 | 0.376 | 19.587 | 96.487 |
| 0.009 | 0 | 0 | 0.007 | 0.389 | 0.073 | 0.074 | 0.003 | 3.997 | 19.037 | 95.896 |
| 0 | 0 | 0.017 | 0.001 | 0.387 | 0.051 | 0 | 0 | 4.111 | 19.588 | 98.206 |
| 0.013 | 0 | 0.051 | 0 | 0.261 | 0.101 | 0 | 0.061 | 3.986 | 19.36 | 98.539 |
| 0.026 | 0 | 0 | 0.05 | 0.559 | 0 | 0.004 | 0.022 | 3.909 | 19.722 | 98.674 |
| 0.003 | 0 | 0 | 0 | 0.209 | 0.056 | 0 | 0.033 | 4.017 | 19.767 | 99.617 |
| 0.021 | 0 | 0.024 | 0.02 | 0.242 | 0.039 | 0.066 | 0.073 | 4.042 | 19.324 | 99.009 |
| 0 | 0 | 0 | 0.041 | 0.082 | 0 | 0 | 0.038 | 3.686 | 18.844 | 98.273 |
| 0 | 0 | 0 | 0.051 | 0.929 | 0.033 | 0 | 0.024 | 3.847 | 19.016 | 97.264 |
| 0 | 0 | 0 | 0.011 | 0.667 | 0.112 | 0.102 | 0.006 | 4.005 | 18.919 | 97.385 |
| 0.022 | 0 | 0 | 0.045 | 0.464 | 0.056 | 0 | 0 | 3.985 | 18.956 | 97.952 |
| 0 | 0 | 0 | 0 | 0.401 | 0 | 0 | 0.018 | 4.052 | 19.527 | 99.303 |
| 0 | 0 | 0 | 0 | 0.823 | 0.006 | 0 | 0.049 | 3.998 | 19.142 | 99.186 |
| 0 | 0 | 0 | 0.044 | 0.559 | 0.078 | 0 | 0 | 3.955 | 19.012 | 98.184 |
| 0.017 | 0 | 0 | 0.004 | 0.726 | 0.039 | 0 | 0.04 | 3.845 | 18.708 | 96.774 |
| 0 | 0 | 0.019 | 0.035 | 1.024 | 0 | 0.067 | 0.024 | 3.979 | 18.426 | 95.615 |
| 0.008 | 0 | 0 | 0.01 | 0.237 | 0.156 | 0 | 0.01 | 3.904 | 18.753 | 97.395 |
| 0.398 | 0 | 0.002 | 0 | 0.508 | 0 | 0.064 | 0.023 | 2.558 | 18.115 | 92.769 |
| 7.975 | 0.056 | 0 | 0.079 | 0.136 | 0 | 0 | 0 | 0.391 | 19.984 | 98.815 |
| 4.564 | 0.017 | 0.043 | 0.041 | 0.124 | 0 | 0 | 0.04 | 0.268 | 20.661 | 97.906 |
| 0 | 0 | 0 | 0.013 | 1.054 | 0 | 0 | 0.057 | 0.514 | 15.057 | 78.153 |
| 5.468 | 0 | 0 | 0.019 | 0.109 | 0.039 | 0 | 0.029 | 0.344 | 20.314 | 97.221 |
| 5.202 | 0.027 | 0.046 | 0.022 | 0.069 | 0 | 0 | 0.025 | 0.246 | 20.765 | 97.595 |
| 12.781 | 0 | 0.152 | 0 | 0.076 | 0 | 0.097 | 0 | 0.139 | 25.39 | 99.043 |
| 1.086 | 0 | 0.034 | 0.017 | 0.354 | 0 | 0.118 | 0 | 0.376 | 18.801 | 98.48 |
| 4.553 | 0 | 0.004 | 0.064 | 0.052 | 0.117 | 0.066 | 0.014 | 0.383 | 19.411 | 93.379 |
| 2.232 | 0.109 | 0 | 0.015 | 0.067 | 0 | 0.183 | 0 | 0.052 | 24.23 | 98.794 |
| 6.27 | 0 | 0 | 0.029 | 0 | 0.151 | 0.137 | 0 | 0.327 | 19.081 | 90.166 |
| 1.845 | 0.478 | 0 | 0.025 | 0.12 | 0 | 0 | 0.015 | 0.053 | 25.486 | 99.056 |
| 0.624 | 0 | 0 | 0.048 | 0.682 | 0 | 0 | 0.069 | 2.923 | 19.836 | 97.603 |
| 5.693 | 0 | 0 | 0.033 | 0.033 | 0 | 0 | 0.005 | 0.369 | 19.573 | 96.883 |
| 0.522 | 0.069 | 0.016 | 0 | 0.446 | 0.131 | 0.043 | 0.003 | 0.459 | 15.5 | 76.639 |
| 0 | 0 | 0 | 0.049 | 0.667 | 0.238 | 0 | 0.029 | 0.635 | 15.992 | 85.393 |
| 0 | 0 | 0.061 | 0.037 | 0.181 | 0.118 | 0.001 | 0 | 3.921 | 18.46 | 95.899 |
| 0.007 | 0 | 0 | 0.075 | 1.138 | 0.106 | 0 | 0.047 | 4.012 | 19.419 | 98.491 |
| 0 | 0.002 | 0 | 0 | 0.994 | 0 | 0 | 0.023 | 3.864 | 19.345 | 97.244 |
| 0.012 | 0 | 0 | 0.027 | 0.067 | 0 | 0.13 | 0 | 4.028 | 18.99 | 98.544 |
| 0 | 0 | 0 | 0.09 | 0.935 | 0 | 0 | 0.015 | 3.983 | 18.996 | 96.836 |
| 6.973 | 0.39 | 0.035 | 0.062 | 0.135 | 0.068 | 0.016 | 0.003 | 0.075 | 25.017 | 99.816 |
| 0.013 | 0.175 | 0 | 0.062 | 0.347 | 0 | 0.049 | 0 | 4.082 | 19.87 | 99.745 |
| 0 | 0 | 0 | 0 | 0.858 | 0 | 0.134 | 0.011 | 3.948 | 18.981 | 95.705 |
| 0 | 0 | 0 | 0.053 | 0.542 | 0 | 0.016 | 0.034 | 1.056 | 15.815 | 79.663 |
| 0 | 0 | 0.001 | 0 | 0.927 | 0 | 0 | 0.027 | 3.971 | 19.129 | 96.063 |

Mineralogical features of the sample, such as zonality, can also be determined via EMPA. The zonality of the grains can be indicative of the geographic origin of the mineral. For instance, regular or irregular zones, zones rich in tantalum and low in niobium, or zones that are patchy/oscillatory vs. homogeneous may indicate that the sample has a specific geographic origin. The degree of alteration of the grains, the presence of inclusions of different minerals, and the presence of intergrowths with other minerals can also be indicative of the geographic origin of the sample.

Further, EMPA can serve as a standardization tool for laser ablation inductively coupled plasma mass spectrometry, which is discussed in more detail below in Step D. Specifically, the major elements obtained via EMPA (e.g., tantalum, niobium, iron, and manganese for columbite-tantalite) can be used as internal reference elements in laser ablation inductively coupled plasma mass spectrometry in order to standardize or normalize the data for trace/minor elements (e.g., lithium (Li), magnesium (Mg), titanium (Ti), tin (Sn), tungsten (W), zirconium (Zr), uranium (U), scandium (Sc), bismuth (Bi), antimony (Sb), yttrium (Y), ytterbium (Yb), hafnium (Hf), lead (Pb), thorium (Th), etc.) and rare earth elements (REE) (e.g., lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu), etc.) in parts per million (ppm).

D. Laser Ablation Inductively Coupled Plasma Mass Spectrometry (106)

After EMPA, the same grains selected above in Step C are analyzed by laser ablation inductively coupled mass spectrometry (LA-ICP-MS) to quantitatively determine the trace/minor elements and REE present in the sample in ppm. LA-ICP-MS enables highly sensitive elemental and isotopic analysis to be performed directly on solid samples. LA-ICP-MS begins with a laser beam focused on the sample surface to generate fine particles—a process known as laser ablation. The ablated particles are then transported to the secondary excitation source of the ICP-MS instrument for digestion and ionization of the sampled mass. The excited ions in the plasma torch are subsequently transferred to a mass spectrometer detector for both elemental and isotopic analysis. An example of a machine that can perform such analysis is the Agilent 7500CE ICP-MS, available from Agilent Technologies (Santa Clara, Calif.), as well as the laser ablation system UP 213.

The results of LA-ICP-MS are the concentration of 40 elements in parts per million (ppm). The concentration of selected minor/trace elements (lithium (Li), magnesium (Mg), titanium (Ti), tin (Sn), tungsten (W), zirconium (Zr), uranium (U), scandium (Sc), antimony (Sb), yttrium (Y), ytterbium (Yb), hafnium (Hf), lead (Pb), thorium (Th)) and rare earth elements (REE) (e.g., lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), plus any major elements or additional elements present are then used for further evaluation. The REE data is normalized to chondrite (according to Nakamura, N., Determination of REE, Ba, Fe, Mg, Na, and K in carbonaceous and ordinary chondrites, Geochimica et Cosomochimica Acta, 38, 757-775 (1974)) and the minor/trace element data is normalized to a global columbite-tantalite group median (CGM) (according to Melcher, F. et al., Tantalum-(niobium-tin) mineralisation in African pegmatites and rare metal granites: Constraints from Ta—Nb oxide mineralogy, geochemistry, and U—Pb geochronology, Ore Geol. Rev. (2013)), where these normalized data are then plotted to diagrams and compared to a database of diagrams for REE and trace/minor elements for verified conflict-free samples from various mine sites.

If a diagram from a sample substantially matches a diagram for a sample that has already been tested and stored in the database, then it can be determined that the geographic origin (mine site) of the sample is same as the geographic origin (mine site) of the database sample. It should be understood that different minerals have different shapes to the REE and trace/minor element curves due to the different rules of element incorporation to the structure, but the proportional enrichment of the elements characteristic for a specific mine site should be generally retained. While major and minor element composition can be highly variable, the enrichment of the ore in a specific REE pattern can be generally the same for samples from the same locality or mine site. Further, good correlation between trace elements can be present on a deposit or district scale.

Figure 5:
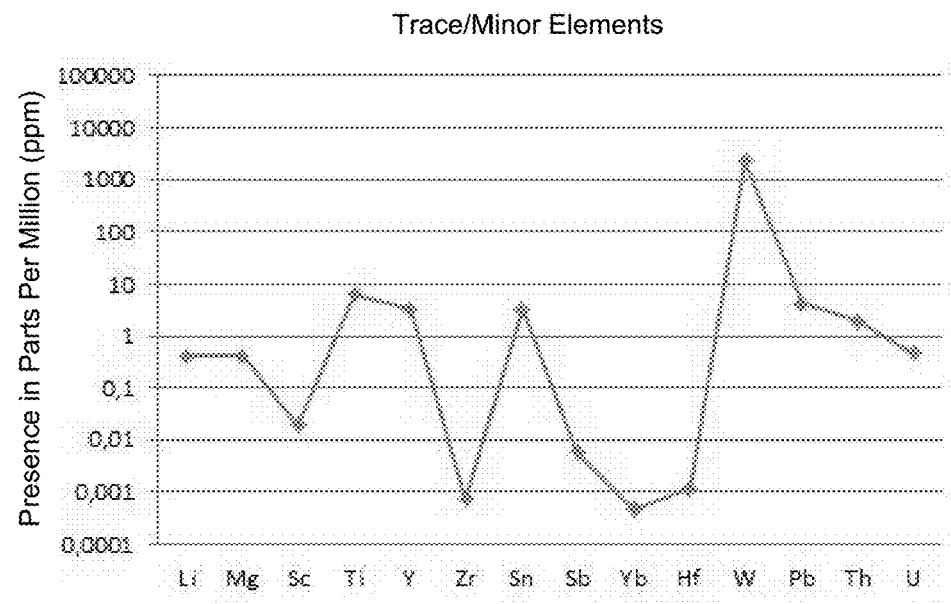
FIG. 5 is a graph showing the amount of various trace/minor elements present in a sample in parts per million as determined by laser ablation inductively coupled plasma mass spectrometry (LA-ICP-MS) after normalization to a global CGM median (according to Melcher, F. et al., Tantalum-(niobium-tin) mineralisation in African pegmatites and rare metal granites: Constraints from Ta—Nb oxide mineralogy, geochemistry, and U—Pb geochronology, Ore Geol. Rev. (2013))
Figure 6:
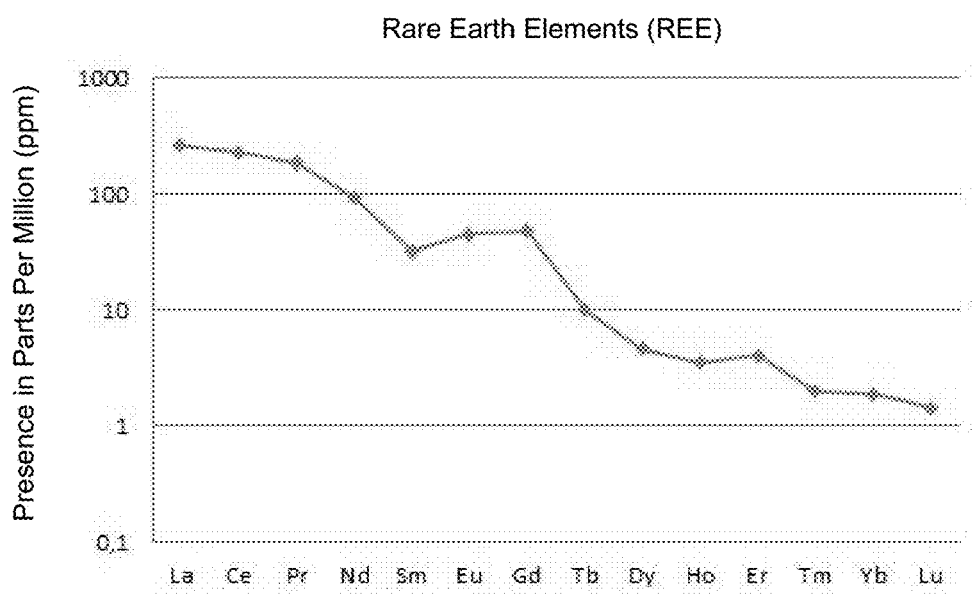
FIG. 6 is a graph showing the amount of rare earth elements (REE) present in a sample in parts per million as determined by laser ablation inductively coupled plasma mass spectrometry (LA-ICP-MS) after chondrite normalization (according to Nakamura, N., Determination of REE, Ba, Fe, Mg, Na, and K in carbonaceous and ordinary chondrites, Geochimica et Cosomochimica Acta, 38, 757-775 (1974))
Figure 7:
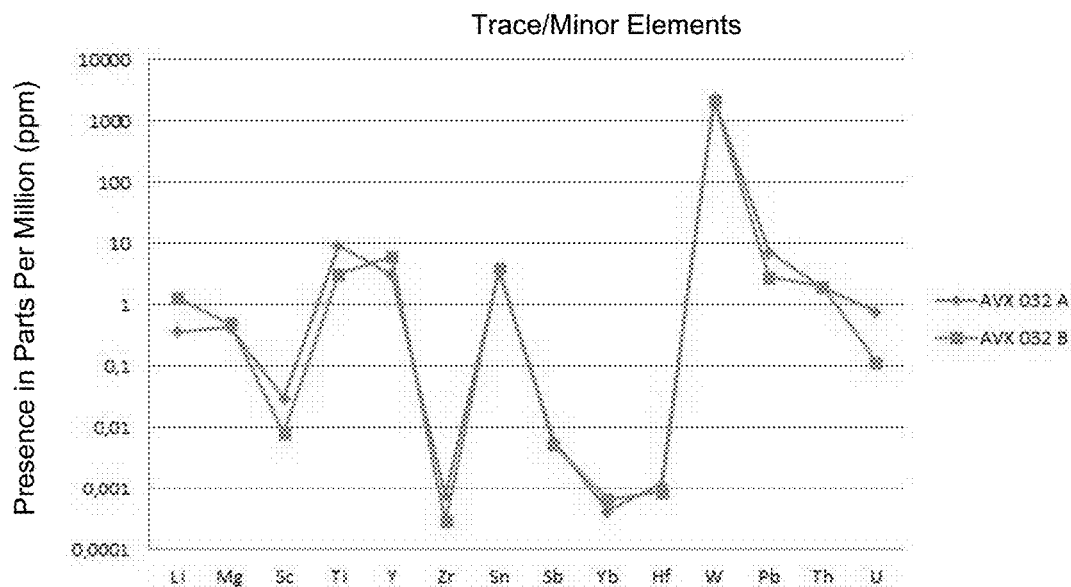
FIG. 7 is a graph comparing two samples from the same mine site showing the reproducibility of trace/minor element analysis via LA-ICP-MS as a tool to determine the geographic origin of a sample.
Figure 8:
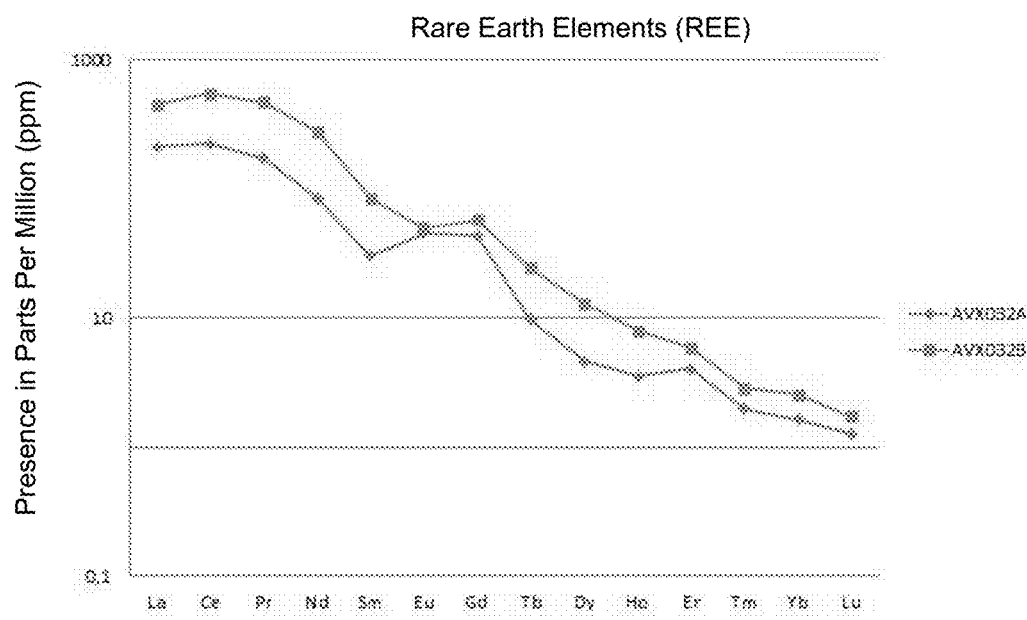
FIG. 8 is graph comparing two samples from the same mine site showing substantially the same amounts of REE present as determined via LA-ICP-MS to show that LA-ICP-MS can be used as a tool to determine the geographic origin of a sample.
Figure 9:
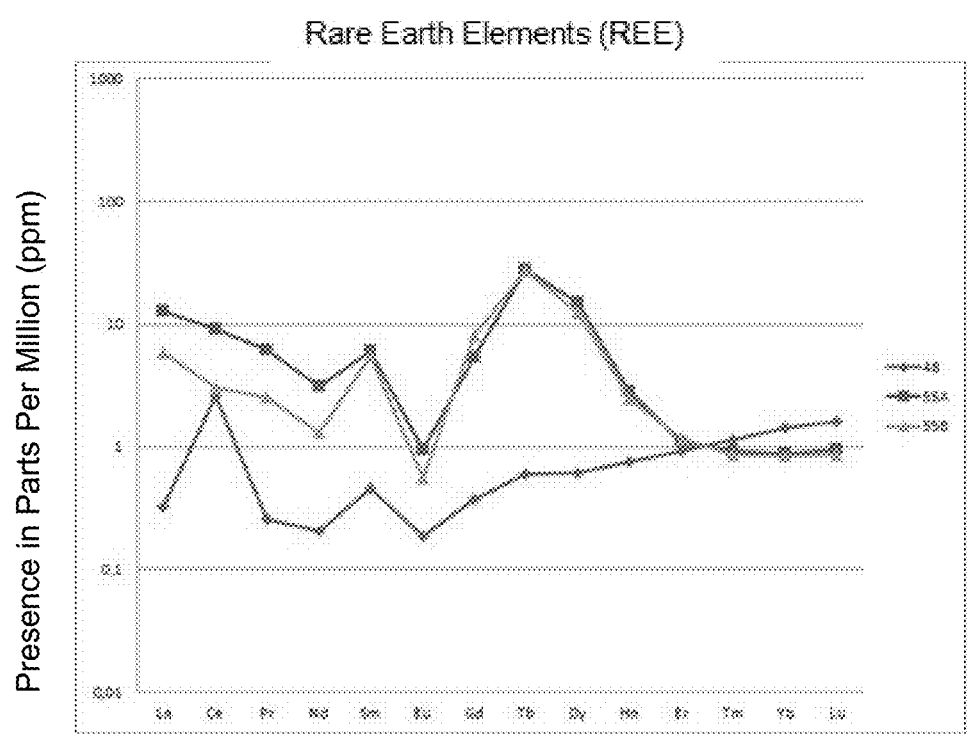
FIG. 9 is a graph comparing one self-collected tantalite sample (sample 48) to two shipment samples (samples 55A and 55B) showing the variability in amounts of REE present determined via LA-ICP-MS to show that LA-ICP-MS can be used as a tool to determine that the two shipped samples are not sourced from the same mine site or geographic origin of as the self-collected sample.

As an example, LA-ICP-MS results for one mine site are shown in FIG. 5 for the trace/minor elements and FIG. 6 for the REE. Meanwhile, FIGS. 7 and 8 show the reproducibility of the LA-ICP-MS trace/minor element and REE analysis by showing the strong correlation between two samples (e.g., samples 32A and 32B) taken from the same microlite mine site. In addition, FIG. 9 demonstrates the ability of the LA-ICP-MS analysis to assist in identifying that shipped samples may not be from a particular mine site. For instance, samples 55A and 55B were said to be from a particular tantalite mine site, but, as shown in the graph, the variations in the amount of REE present in the shipped samples 55A and 55B compared to the previously analyzed and validated sample 48 indicate that extraneous material of unknown origin may be have been added to samples 55A and 55B, such that it cannot be verified that the samples include material from a conflict-free mine site. Thus, the variations in the amount of REE present in parts per million (ppm) depending on the mine site that can be detected via LA-ICP-MS means that LA-ICP-MS analysis can be used as a tool to determine the particular mine site from which a sample is obtained, where it can be further determined if the sample is in fact from a conflict-free mine site and geographic region. In other words, LA-ICP-MS in conjunction with the other steps discussed above can be used to verify that minerals delivered from specific mine sites that have been independently validated as conflict-free do in fact originate from the specific mine site as claimed.

E. Geochronology Analysis

Although not shown in FIG. 1, geochronology analysis can also be conducted to distinguish the geographic origin of a mineral sample based on the age of the ore concentrate using the Uranium-Lead (U—Pb) dating method, as tantalum ores usually contain high levels of uranium and low levels of lead and are thus suitable for U—Pb radiometric dating. In situ analysis by LA-ICP-MS can be used to acquire the age of the minerals in a sample of mixed concentrates (e.g., columbite-tantalite, microlite, or accompanying minerals zircon or monazite), and the age can be used for comparison to ages stored for various samples in a database obtained from validated conflict-free mine sites, where a sample having a similar age to a sample from a validated conflict-free mine site may be from the validated conflict-free mine site.

Uranium-lead (U—Pb) dating is one of the oldest and most refined of the radiometric dating schemes. It can be used to date rocks that formed from about 1 million years to over 4.5 billion years ago with routine precisions in the 0.1% to 1% range. The uranium-lead dating method relies on two separate decay chains, the uranium series from $^{238}$U to $^{206}$Pb, with a half-life of 4.47 billion years and the actinium series from $^{235}$U to $^{207}$Pb, with a half-life of 710 million years. These uranium to lead decay routes occur via a series of alpha (and beta) decays, in which $^{238}$U with daughter nuclides undergo eight total alpha and six beta decays whereas $^{235}$U with daughters only experience seven alpha and four beta decays. The existence of two parallel uranium-lead decay routes ($^{238}$U to $^{206}$Pb and $^{235}$U to $^{207}$Pb) leads to multiple dating techniques within the overall U—Pb system. The term U—Pb dating normally described herein refers to the coupled use of both decay schemes.

F. Chemical Assays

Although not shown in FIG. 1, one or more chemical assays can be performed to aid in determining the source of the unverified mineral sample. For example, one or more chemical assays can be performed to determine the amount of uranium, thorium, or tantalum present in the unverified mineral sample, where the presence of uranium, thorium, or tantalum in certain amounts can help determine if the unverified mineral sample is sourced from a conflict-free mine site or geographic region. Such assays can include inductively coupled plasma optical emission spectroscopy (ICP-OES) testing or inductively coupled plasma mass spectroscopy (ICP-MS) testing. For example, if tantalum is present as determined via ICP-OES testing above a certain threshold (e.g., above 25 wt. %), or if a tantalum oxide (e.g., $Ta_2O_5$) is present above a certain threshold (e.g., above 30 wt. %), there is an indication that microlite may be present in the sample, which means that further analysis should be conducted to ensure that the sample is from a conflict-free mine site. Additionally, if a uranium oxide (e.g., $U_3O_8$) and/or a thorium oxide (e.g., $ThO_2$) is present as determined via ICP-MS testing above a certain threshold (e.g., above 1 wt. %), there is also an indication that microlite may be present in the sample, which means that further analysis should be conducted to ensure that the sample is from a conflict-free mine site.

G. Analysis to Determine if Sample is from a Conflict-Free Mine Site (107)

After the steps described above are completed, the data from each of the steps for a particular unverified mineral sample is compared to data stored in a database, where the data stored in the database corresponds with the same test results for mineral samples from mine sites that have been previously verified as conflict-free. The data is in the form of raw data, calculated or normalized data, tables, charts, and diagrams for individual samples or comparisons of samples, AM images, calculated ages, and mineralogical study documents. Various statistical methods can then be applied to the data for data processing such as univariate analysis and multivariate analysis. Univariate analysis can be applied for the characterization and description of element distribution within a sample (e.g., distribution shape, multimodality, etc.), and brother samples can be identified using Wilcoxon and Kolmogorov-Smirnov tests. Meanwhile, multivariate analysis can be applied to determine dependencies between elements in a sample (e.g., correlation, graphical methods), unsupervised classification methods (e.g., hierarchical and fuzzy cluster analysis, principal component analysis, Kohonen maps (SOM), classification and regression trees (CART), and artificial neural networks (ANN)).

The final results of the statistical evaluation comparing an unverified sample to the database of verified conflict-free samples is the final number in percent (%) that corresponds to the conformity of the unverified sample and a verified conflict-free sample from the database. The higher the percentage match (probability match) or correlation, then the more likely it is that the unverified sample is from the same, conflict-free mine site as the verified sample. For instance, a percent match between an unverified sample and a verified sample of at least 50%, such as from about 50% to 100%, such as from about 60% to 100%, such as from about 65% to about 100%, such as from about 70% to about 100%, indicates that the unverified sample and the verified sample originate from the same conflict-free mine site or mine sites from the same geographic region.

Figure 10:
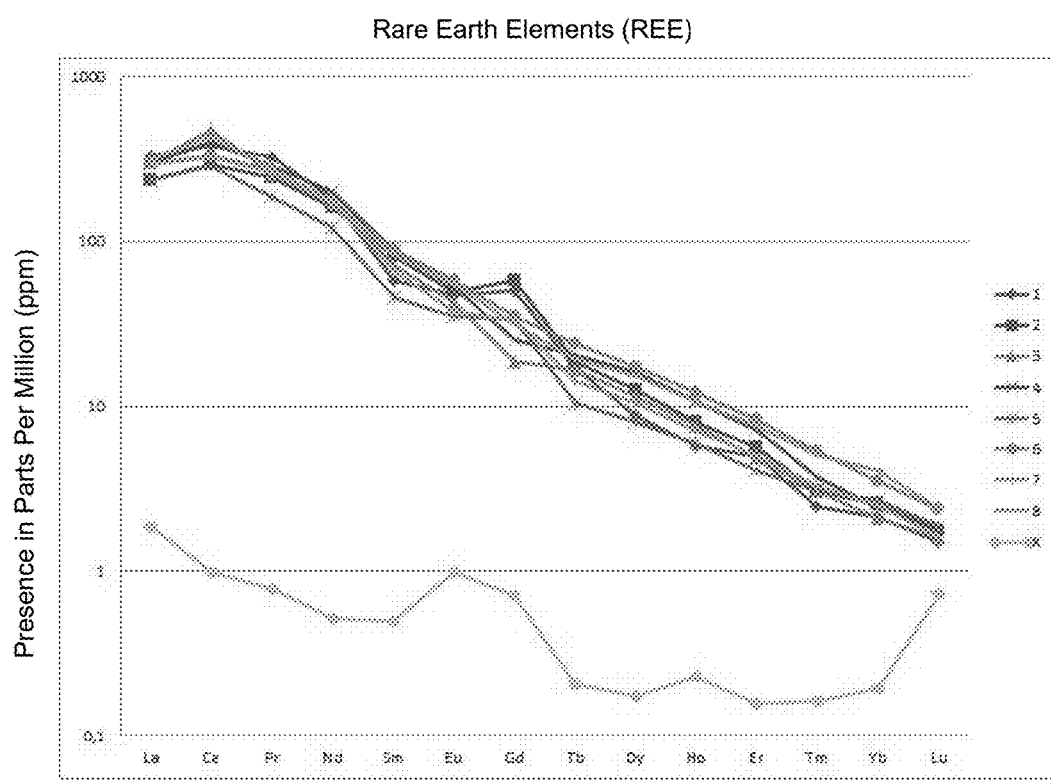
FIG. 10 is a graph showing how a mineral sample received from an unknown or unverified location can be compared to eight samples verified to be from the same mine site in order to determine that the unverified mineral sample is not sourced from the same mine site as the eight samples due to the variability in amounts of REE present determined via LA-ICP-MS, which demonstrates that LA-ICP-MS can be used as a tool to determine the geographic origin of a sample.

For example, FIG. 10 is a graph showing how a mineral sample X from an unknown or unverified location can be compared to eight samples (samples 1-8) known to be sourced from the same mine site or region and stored in a database in order to determine that the unverified mineral sample is not sourced from the same mine site or region as samples 1-8. Such a determination is made by comparing the variability in the REE concentration in parts per million as determined via LA-ICP-MS. As can been seen from FIG. 10, it cannot be determined that sample X is sourced from the same mine site or geographic region associated with samples 1-8. After statistical analysis reviewing the amount of various minerals present (e.g., major elements, trace/minor elements, REE, etc.), it is determined that there is a low probability that sample X is from the same mine site or geographic region associated with samples 1-8 stored in the database. The ability to make such a determination demonstrates that the mineral source identification tools and methods of the present application can be used to identify the particular mine site or multiple mine sites from which a mineral sample is received and to mitigate risk of sourcing minerals (e.g., valve metals) from unapproved mine sites or mine sites in conflict areas.

Figure 11:
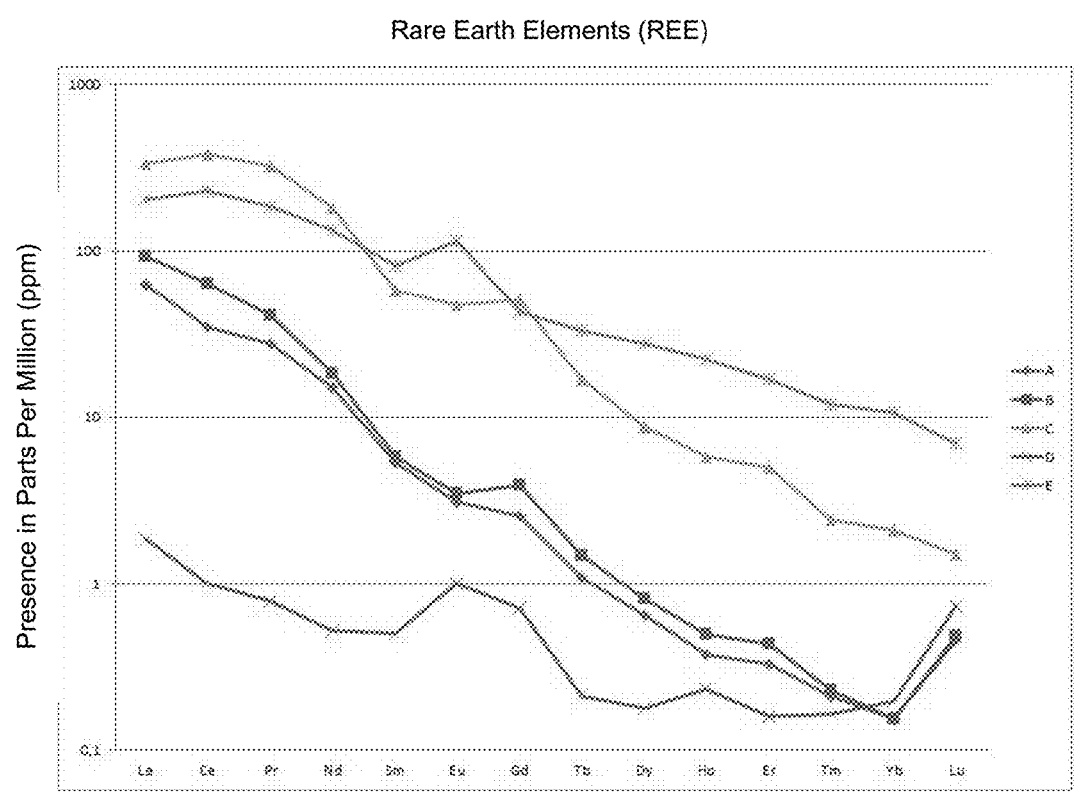
FIG. 11 is a graph comparing the REE concentration in parts per millions for four test samples compared to the REE concentration in parts per million for a verified sample obtained from a known location (e.g., an approved mine site), as determined via LA-ICP-MS to show that LA-ICP-MS can be used as a tool to determine the geographic origin of a sample.

Meanwhile, FIG. 11 is a graph comparing the REE concentration in parts per millions for four test microlite samples (samples B, C, D, and E) compared to the REE concentration in parts per million for a verified sample (sample A) obtained from a known mine site or geographic region, as determined via LA-ICP-MS to show that LA-ICP-MS can be used as a tool to determine the geographic origin of a particular sample by comparing the concentration of REE present in the sample with the concentration of REE for samples from known mine sites or geographic regions. As shown, sample B corresponds closely with sample A, while samples C, D, and E contain substantially different levels of REE. After statistical analysis using the Kolmogorov-Smirnov test, it is determined that there is a 80% probability that sample B is from the same mine site associated with sample A, while it cannot be verified that samples C, D, and E have been obtained from the same mine site associated with sample A, as there is only a 30% correlation between sample A and sample C, a 45% correlation between sample A and sample D, and a 3% correlation between sample A and sample E.

In addition, Table 3 is chart comparing the correlation or similarity between microlite samples to determine the probability that an unknown sample was sourced from one of four verified/known mine sites. Specifically, twenty two samples received were processed to determine the elemental distribution within the grains in each sample, the elemental analysis information was determined, and the percent correlation or similarity to various samples from verified/known mine sites was determined using the Kolmogorov-Smirnov test. A % correlation of less than 50% indicates that an unknown sample is not sourced from a known mine site, a % correlation between 50-60% indicates that there is a possibility that an unknown sample is sourced from a known mine site (although additional verification should be completed), and a % correlation greater than 60% indicates that an unknown sample is sourced from a known mine site.

Referring to Table 3 below, it can be determined that unknown samples 2, 4, 8, 12-18, and 21-22 are sourced from mine site 1, unknown samples 5-7, 10, and 20 are sourced from mine site 2, and unknown sample 1 is sourced from mine site 3.

TABLE 3

Probability (%) That Unknown Sample Sourced from Verified Mine Site Based on Element Distribution in Analyzed Grains Using the Kolmogorov-Smirnov Test Probability (%) That Unknown Sample Sourced from Verified Mine Site Based on Element Distribution in Analyzed Grains - Kolmogorov-Smirnov Test

| Sample Name | Verified Sample 1 Mine 1 | Verified Sample 2 Mine 1 | Verified Sample Mine 2 | Verified Sample Mine 3 | Verified Sample Mine 4 |
|---|---|---|---|---|---|
| Unknown Sample 1 | 43 | 37 | 23 | 58 | 1 |
| Unknown Sample 2 | 72 | 70 | 30 | 40 | 3 |
| Unknown | 28 | 23 | 9 | 30 | 0 |

TABLE 3-continued

Probability (%) That Unknown Sample Sourced from Verified Mine Site Based on Element Distribution in Analyzed Grains Using the Kolmogorov-Smirnov Test
Probability (%) That Unknown Sample Sourced from Verified Mine Site Based on Element Distribution in Analyzed Grains - Kolmogorov-Smirnov Test

| Sample Name | Verified Sample 1 Mine 1 | Verified Sample 2 Mine 1 | Verified Sample Mine 2 | Verified Sample Mine 3 | Verified Sample Mine 4 |
|---|---|---|---|---|---|
| Sample 3 |  |  |  |  |  |
| Unknown Sample 4 | 80 | 76 | 29 | 42 | 3 |
| Unknown Sample 5 | 17 | 21 | 69 | 18 | 34 |
| Unknown Sample 6 | 21 | 24 | 71 | 22 | 32 |
| Unknown Sample 7 | 14 | 17 | 67 | 16 | 35 |
| Unknown Sample 8 | 63 | 50 | 21 | 43 | 2 |
| Unknown Sample 9 | 40 | 43 | 44 | 33 | 21 |
| Unknown Sample 10 | 13 | 14 | 60 | 15 | 34 |
| Unknown Sample 11 | 15 | 18 | 59 | 14 | 46 |
| Unknown Sample 12 | 69 | 56 | 22 | 45 | 1 |
| Unknown Sample 13 | 64 | 54 | 23 | 45 | 3 |
| Unknown Sample 14 | 61 | 50 | 17 | 41 | 1 |
| Unknown Sample 15 | 61 | 51 | 22 | 41 | 2 |
| Unknown Sample 16 | 62 | 49 | 19 | 47 | 1 |
| Unknown Sample 17 | 61 | 49 | 21 | 42 | 2 |
| Unknown Sample 18 | 65 | 52 | 25 | 47 | 5 |
| Unknown Sample 19 | 50 | 44 | 25 | 44 | 4 |
| Unknown Sample 20 | 18 | 23 | 66 | 20 | 27 |
| Unknown Sample 21 | 66 | 59 | 24 | 44 | 2 |
| Unknown Sample 22 | 63 | 55 | 35 | 48 | 13 |

If it cannot be verified that the unverified sample is from the mine site (e.g., a conflict-free mine site or approved mine site) from which it is claimed to originate, the sample is returned and not used in the production of the electrolytic capacitors contemplated by the present invention, as described in step 108. Meanwhile, if it can be verified that the unverified sample is from the conflict-free mine site from which it is claimed to originate, the sample can be used to make an anode for the electrolytic capacitor as contemplated by the present invention and as described in step 109.

Figure 2:
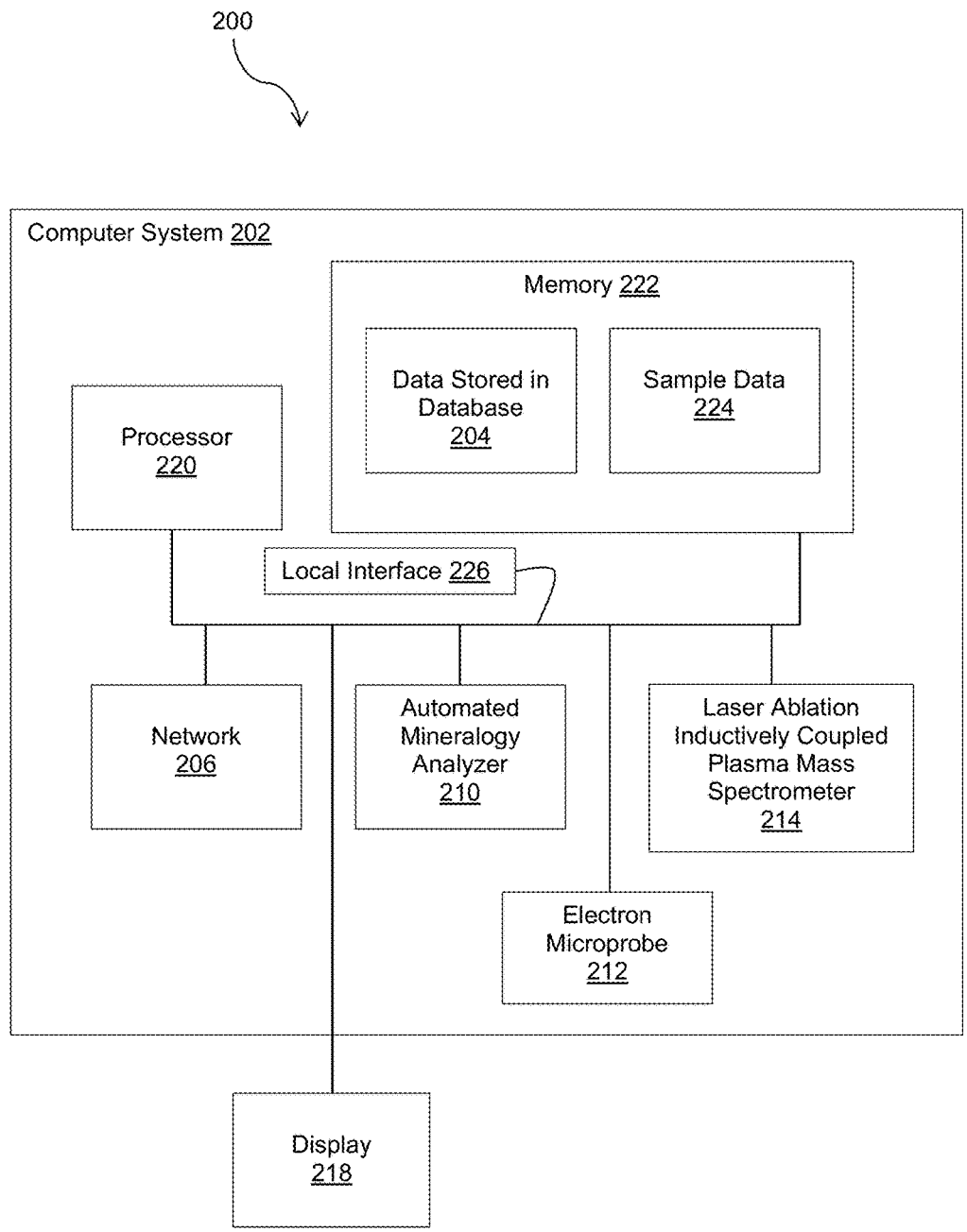
FIG. 2 is a block diagram of a system used in determining the geographic origin of a mineral sample.

The analysis steps described in FIG. 1 and set forth above can be carried out using the apparatus 200 shown in FIG. 2. The apparatus 200 includes a computer system 202. The computer system 202 may include one or more processors 220 that are in communication with one or more memory devices 222. The computer system 202 may include a local communication interface 226 for the components in the computer system 202. For example, the local communication interface 226 may be a local data bus or any related address or control busses.

The memory device 222 may contain modules that are executable by the processor(s) 220 and data for the modules. Located in the memory device 222 are data stored in the database 204 from previous analyses related to samples from mine sites that have been validated or verified as conflict-free. Sample data 224 is also located in the memory device 222 for storing data related to the unverified samples currently being tested. Although not shown, the memory device 222 can also store dated related to other applications along with an operating system that is executable by the processor(s).

Other applications may also be stored in the memory device 222 and may be executable by the processor(s) 220. Components discussed in this description may be implemented in the form of software using high programming level languages that are compiled, interpreted or executed using a hybrid of the methods.

The computer system 202 may also have access to I/O (input/output) devices that are usable by the computing devices. An example of an I/O device is a display screen 218 that is available to display output from the computer system 202. Other known I/O devices may be used with the computer system 202 as desired. One or more networking devices 206 and similar communication devices may be included in the computer system 202. Further, an automated mineralogy analyzer 210, an electron microscope 212, and a laser ablation inductively coupled plasma mass spectrophotometer 214 can be directly connected to the networking device 206. The networking device 206 may be wired or wireless networking devices that connect to the internet, a LAN, WAN, or other computing network.

The components that are shown as being stored in the memory device 222 may be executed by the processor 220. The term "executable" may mean a program file that is in a form that may be executed by a processor. For example, a program in a higher level language may be compiled into machine code in a format that may be loaded into a random access portion of the memory device and executed by the processor 220, or source code may be loaded by another executable program and interpreted to generate instructions in a random access portion of the memory 222 to be executed by a processor 220. The executable program may be stored in any portion or component of the memory device 222. For example, the memory device 222 may be random access memory (RAM), read only memory (ROM), flash memory, a solid state drive, memory card, a hard drive, optical disk, floppy disk, magnetic tape, or any other memory components.

The processor 220 may represent multiple processors and the memory 222 may represent multiple memory units that operate in parallel to the processing circuits. This may provide parallel processing channels for the processes and data in the system 202. The local interface 226 may be used as a network to facilitate communication between any of the multiple processors and multiple memories. The local interface may use additional systems designed for coordinating communication such as load balancing, bulk data transfer, and similar systems.

Once a sample is verified as originating from a conflict-free mine site, the valve metal from the mineral sample can be utilized to form an electrolytic capacitor, as described in more detail below in sections III and IV.

Figure 14:
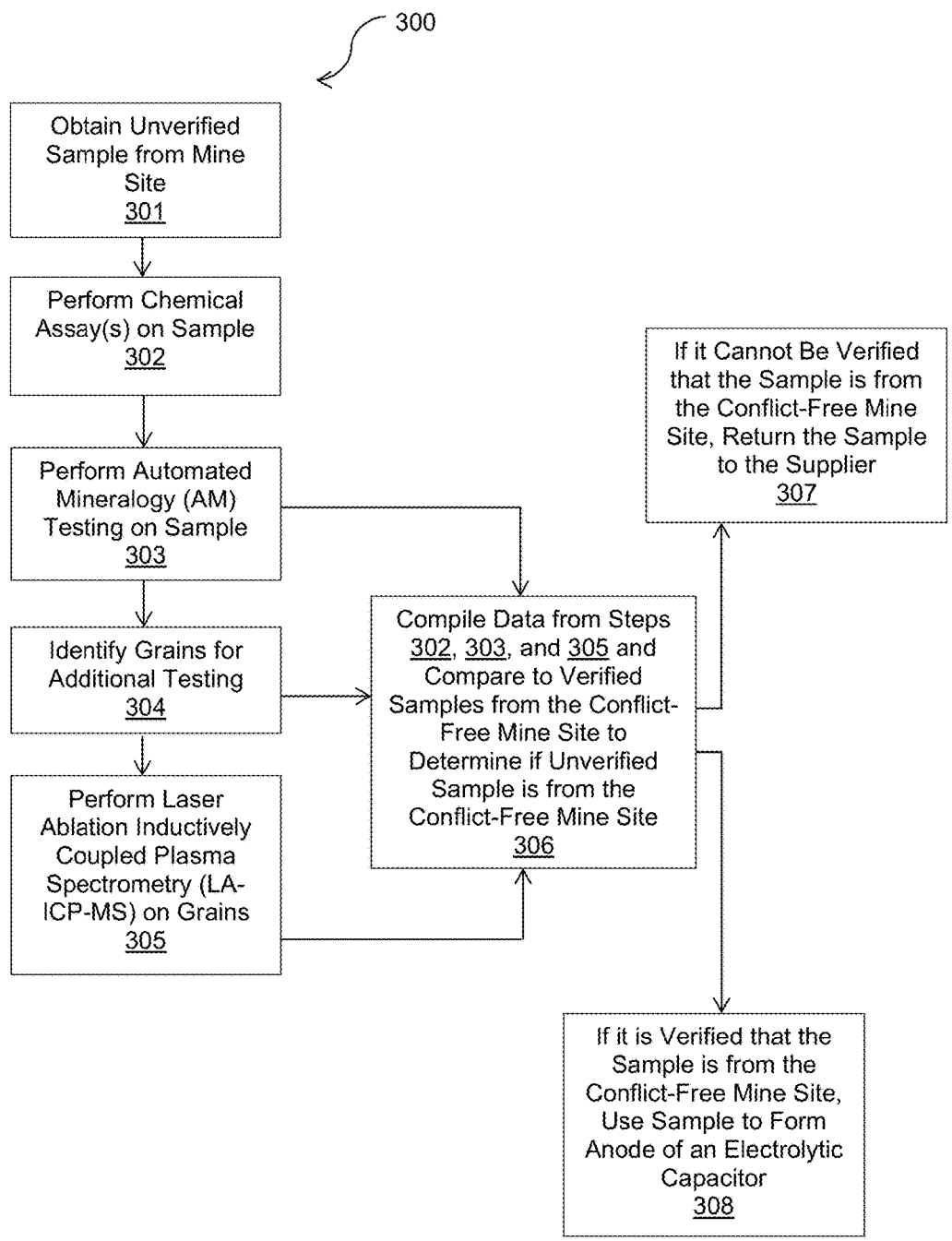
FIG. 14 is a block diagram illustrating another method for determining the geographic origin of a mineral sample.

II. Alternative Method for Determining if a Valve Metal Sample Originates from a Conflict-Free Mine Site In addition to the method 100 described above in Section I, the present invention also contemplates alternative methods, such as method 300, shown in FIG. 14, for verifying the source of a valve metal sample. The method 300 of forming an electrolytic capacitor from a conflict-free valve metal powder includes first obtaining an unverified sample (i.e., a sample that has not been verified as conflict free) from a mine site, where the sample may have been independently described as conflict-free by another party (step 301). The sample can be self-collected as a heavy-mineral panned concentrate directly at the mine site to be sure about the origin of the sample and to collect the sample before any further processing is carried out to preserve the complete heavy mineral association.

Next, in step 302, one or more chemical assays can be performed to aid in determining the source of the unverified mineral sample. For example, one or more chemical assays can be performed to determine the amount of uranium, thorium, or tantalum present in the unverified mineral sample, where the presence of uranium, thorium, or tantalum in certain amounts can help determine if the unverified mineral sample is sourced from a conflict-free mine site or geographic region. Such assays can include inductively coupled plasma optical emission spectroscopy (ICP-OES) testing or inductively coupled plasma mass spectroscopy (ICP-MS) testing. For example, if tantalum is present as determined via ICP-OES testing above a certain threshold (e.g., above 25 wt. %), or if a tantalum oxide (e.g., $Ta_2O_5$) is present above a certain threshold (e.g., above 30 wt. %), there is an indication that microlite may be present in the sample, which means that further analysis should be conducted to ensure that the sample is from a conflict-free mine site. Additionally, if a uranium oxide (e.g., $U_3O_8$) and/or a thorium oxide (e.g., $ThO_2$) is present as determined via ICP-MS testing above a certain threshold (e.g., above 1 wt. %), there is also an indication that microlite may be present in the sample, which means that further analysis should be conducted to ensure that the sample is from a conflict-free mine site.

Then, in step 303, a portion of the sample (which has been formed to a polished epoxy and coated with a carbon layer as described above with respect to method 100) can be scanned via automated mineralogy (AM) to determine the specific minerals present in the sample as well as the prevalence and distribution of each of the minerals in the polished section, where samples taken from the same mine site and depth should include the same minerals and at substantially the same prevalence and distribution. For instance, the amount of microlite can be determined, along with other elements. For example, if the amount of microlite present is above a certain threshold (e.g., above 3 wt. %), further analysis should be conducted to ensure that the sample is from a conflict-free mine site. In addition, if samples from the same mine site and depth do not include substantially the same minerals with substantially the same prevalence and distribution after AM testing, then it is possible that the supplier added extraneous material to the sample before shipment. Thereafter, in step 304, grains from the polished section of the sample are selected for further analysis. For example, 50 grains containing tantalum, as determined from the AM scan, can be selected for further analysis.

Further, in step 305, laser ablation inductively coupled plasma spectrometry (LA-ICP-MS) is performed on selected grains to determine the trace/minor elements and rare earth elements present in the grains in parts per million (ppm). If the amounts of trace/minor elements and/or rare earth elements match the amounts obtained for one or more samples from a verified mine site, then it can be determined that the unverified sample is sourced from the verified mine site.

Next, in step 306, data from steps 302, 303, and/or 306 is then compiled to determine if the characteristics of the unverified sample from the allegedly conflict-free mine site substantially match the characteristics of verified samples from one or more conflict-free mine sites via any one of the statistical analysis methods discussed above with respect to method 100. If it cannot be verified that the sample originated from and was sourced from a validated conflict-free mine site, the sample is returned to the supplier in step 307. Meanwhile, if it can be verified that the unverified sample in fact originated and was sourced from a validated conflict-free mine site, the now verified sample can be used to form the electrolytic capacitor of the present invention in step 308.

III. Solid Electrolytic Capacitor Containing a Valve Metal Sourced from a Conflict-Free Mine Site After verifying that the previously unverified mineral sample containing a valve metal (e.g., tantalum, niobium, etc.) is sourced from a conflict-free mine site in step 109 or step 308 as described above, the valve metal of interest in the mineral sample can be separated from other components in the sample and formed into a powder to use in the making of an anode for an electrolytic capacitor. In one particular embodiment, the anode can be used in forming a solid electrolytic capacitor that also includes a dielectric and solid electrolyte. The various components of the solid electrolytic capacitor are discussed in more detail below.

A. Anode

Once it is verified that the valve metal is sourced from a conflict-free mine site, the valve metal can then be formed into a powder to form a porous anode body for use in the solid electrolytic capacitor of the present invention. The porous anode body is typically formed from a valve metal composition having a high specific charge, such as about 5,000 µF*V/g or more, in some embodiments about 10,000 µF*V/g or more, in some embodiments about 20,000 µF*V/g or more. Such powders typically have a specific charge of from about 10,000 to about 600,000 µF*V/g, in some embodiments from about 40,000 to about 500,000 µF*V/g, in some embodiments from about 50,000 to about 400,000 µF*V/g, in some embodiments from about 70,000 to about 350,000 µF*V/g, and in some embodiments, from about 150,000 to about 300,000 µF*V/g. The valve metal composition contains a valve metal (i.e., a metal that is capable of oxidation) or a valve metal-based compound, such as tantalum, niobium, aluminum, hafnium, titanium, alloys thereof, oxides thereof, nitrides thereof, and so forth. Examples of such valve metal oxides are described in U.S. Pat. No. 6,322,912 to Fife; U.S. Pat. No. 6,391,275 to Fife et al.; U.S. Pat. No. 6,416,730 to Fife et al.; U.S. Pat. No. 6,527,937 to Fife; U.S. Pat. No. 6,576,099 to Kimmel, et al.; U.S. Pat. No. 6,592,740 to Fife, et al.; and U.S. Pat. No. 6,639,787 to Kimmel, et al.; and U.S. Pat. No. 7,220,397 to Kimmel, et al., as well as U.S. Patent Application Publication Nos. 2005/0019581 to Schnitter; 2005/0103638 to Schnitter, et al.; 2005/0013765 to Thomas, et al., all of which are incorporated herein in their entirety by reference thereto for all purposes.

To form the anode, a powder of the valve metal composition is generally employed. The powder may contain particles any of a variety of shapes, such as nodular, angular, flake, etc., as well as mixtures thereof. Particularly suitable powders are tantalum powders available from Cabot Corp. (e.g., C255 flake powder, TU4D flake/nodular powder, etc.) and Heraeus (e.g., NH175 nodular powder). Although not required, the powder may be agglomerated using any technique known in the art, such as through heat treatment. Prior to forming the powder into the shape of an anode, it may also be optionally mixed with a binder and/or lubricant to ensure that the particles adequately adhere to each other when pressed to form the anode body. The resulting powder may then be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing.

Regardless of its particular composition, the powder is compacted around the anode lead so that at least a portion of the anode lead assembly extends from the compacted porous anode body. In one particular embodiment, a press mold may be employed that includes a die having two or more portions (e.g., upper and lower portions). During use, the portions of the die may be placed adjacent to each other so that their walls are substantially aligned to form a die cavity having the desired shape of the anode. Before, during, and/or after loading a certain quantity of powder into the die cavity, the anode lead may be embedded therein. The die may define a single or multiple slots that allow for the insertion of the anode lead. If more than one anode lead is employed, the anode lead can be placed in close proximity to each other in order to be sinter-bonded, although this is not required. After filling the die with powder and embedding the anode lead(s) therein, the die cavity may then be closed and subjected to compressive forces by a punch. Typically, the compressive forces are exerted in a direction that is either generally parallel or generally perpendicular to the length "of the anode lead, which extends along a longitudinal axis. This forces the particles into close contact with the anode lead and creates a strong anode lead-to-powder bond.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al., which is incorporated herein in its entirety by reference thereto for all purposes. Thereafter, the porous anode body 33 is sintered to form a porous, integral mass. The pellet is typically sintered at a temperature of from about 1200° C. to about 2000° C., in some embodiments from about 1300° C. to about 1900° C., and in some embodiments, from about 1500° C. to about 1800° C., for a time of from about 5 minutes to about 100 minutes, and in some embodiments, from about 30 minutes to about 60 minutes. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

B. Dielectric

Once constructed, a dielectric layer may be formed by anodically oxidizing ("anodizing") the sintered anode body. The dielectric may be formed by anodically oxidizing ("anodizing") the sintered anode so that a dielectric layer is formed over and/or within the anode body. For example, a tantalum (Ta) anode may be anodized to tantalum pentoxide ($Ta_2O_5$). Typically, anodization is performed by initially applying an electrolyte to the anode, such as by dipping anode into the electrolyte. The electrolyte is generally in the form of a liquid, such as a solution (e.g., aqueous or non-aqueous), dispersion, melt, etc. A solvent is generally employed in the electrolyte, such as water (e.g., deionized water); ethers (e.g., diethyl ether and tetrahydrofuran); alcohols (e.g., methanol, ethanol, n-propanol, isopropanol, and butanol); triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. The solvent may constitute from about 50 wt. % to about 99.9 wt. %, in some embodiments from about 75 wt. % to about 99 wt. %, and in some embodiments, from about 80 wt. % to about 95 wt. % of the electrolyte. Although not necessarily required, the use of an aqueous solvent (e.g., water) is often desired to help achieve the desired oxide. In fact, water may constitute about 50 wt. % or more, in some embodiments, about 70 wt. % or more, and in some embodiments, about 90 wt. % to 100 wt. % of the solvent(s) used in the electrolyte.

The electrolyte is ionically conductive and may have an ionic conductivity of about 1 milliSiemens per centimeter ("mS/cm") or more, in some embodiments about 30 mS/cm or more, and in some embodiments, from about 40 mS/cm to about 100 mS/cm, determined at a temperature of 25° C. To enhance the ionic conductivity of the electrolyte, a compound may be employed that is capable of dissociating in the solvent to form ions. Suitable ionic compounds for this purpose may include, for instance, acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, dodecylsulfonic acid, dodecylbenzenesulfonic acid, etc.; polymeric acids, such as poly(acrylic) or poly (methacrylic) acid and copolymers thereof (e.g., maleic-acrylic, sulfonic-acrylic, and styrene-acrylic copolymers), carageenic acid, carboxymethyl cellulose, alginic acid, etc.; and so forth. The concentration of ionic compounds is selected to achieve the desired ionic conductivity. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the electrolyte. If desired, blends of ionic compounds may also be employed in the electrolyte.

A current is passed through the electrolyte to form the dielectric layer. The value of voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the surface of the anode. Of course, other known methods may also be employed, such as pulse or step potentiostatic methods. The voltage typically ranges from about 4 to about 200 V, and in some embodiments, from about 9 to about 100 V. During anodic oxidation, the electrolyte can be kept at an elevated temperature, such as about 30° C. or more, in some embodiments from about 40° C. to about 200° C., and in some embodiments, from about 50° C. to about 100° C. Anodic oxidation can also be done at ambient temperature or lower. The resulting dielectric layer may be formed on a surface of the anode and within its pores.

Although not required, in certain embodiments, the dielectric layer may possess a differential thickness throughout the anode body in that it possesses a first portion that overlies an external surface of the anode body and a second portion that overlies an interior surface of the anode body. In such embodiments, the first portion is selectively formed so that its thickness is greater than that of the second portion. It should be understood, however, that the thickness of the dielectric layer need not be uniform within a particular region. Certain portions of the dielectric layer adjacent to the external surface may, for example, actually be thinner than certain portions of the layer at the interior surface, and vice versa. Nevertheless, the dielectric layer may be formed such that at least a portion of the layer at the external surface has a greater thickness than at least a portion at the interior surface. Although the exact difference in these thicknesses may vary depending on the particular application, the ratio of the thickness of the first portion to the thickness of the second portion is typically from about 1.2 to about 40, in some embodiments from about 1.5 to about 25, and in some embodiments, from about 2 to about 20.

To form a dielectric layer having a differential thickness, a multi-stage process is generally employed. In each stage of the process, the sintered anode body is anodically oxidized ("anodized") to form a dielectric layer (e.g., tantalum pentoxide). During the first stage of anodization, a relatively small forming voltage is typically employed to ensure that the desired dielectric thickness is achieved for the inner region, such as forming voltages ranging from about 1 to about 90 volts, in some embodiments from about 2 to about 50 volts, and in some embodiments, from about 5 to about 20 volts. Thereafter, the sintered body may then be anodically oxidized in a second stage of the process to increase the thickness of the dielectric to the desired level. This is generally accomplished by anodizing in an electrolyte at a higher voltage than employed during the first stage, such as at forming voltages ranging from about 50 to about 350 volts, in some embodiments from about 60 to about 300 volts, and in some embodiments, from about 70 to about 200 volts. During the first and/or second stages, the electrolyte may be kept at a temperature within the range of from about 15° C. to about 95° C., in some embodiments from about 20° C. to about 90° C., and in some embodiments, from about 25° C. to about 85° C.

The electrolytes employed during the first and second stages of the anodization process may be the same or different. Typically, however, it is desired to employ different solutions to help better facilitate the attainment of a higher thickness at the outer portions of the dielectric layer. For example, it may be desired that the electrolyte employed in the second stage has a lower ionic conductivity than the electrolyte employed in the first stage to prevent a significant amount of oxide film from forming on the internal surface of anode body. In this regard, the electrolyte employed during the first stage may contain an acidic compound, such as hydrochloric acid, nitric acid, sulfuric acid, phosphoric acid, polyphosphoric acid, boric acid, boronic acid, etc. Such an electrolyte may have an electrical conductivity of from about 0.1 to about 100 mS/cm, in some embodiments from about 0.2 to about 20 mS/cm, and in some embodiments, from about 1 to about 10 mS/cm, determined at a temperature of 25° C. The electrolyte employed during the second stage typically contains a salt of a weak acid so that the hydronium ion concentration increases in the pores as a result of charge passage therein. Ion transport or diffusion is such that the weak acid anion moves into the pores as necessary to balance the electrical charges. As a result, the concentration of the principal conducting species (hydronium ion) is reduced in the establishment of equilibrium between the hydronium ion, acid anion, and undissociated acid, thus forms a poorer-conducting species. The reduction in the concentration of the conducting species results in a relatively high voltage drop in the electrolyte, which hinders further anodization in the interior while a thicker oxide layer is being built up on the outside to a higher formation voltage in the region of continued high conductivity. Suitable weak acid salts may include, for instance, ammonium or alkali metal salts (e.g., sodium, potassium, etc.) of boric acid, boronic acid, acetic acid, oxalic acid, lactic acid, adipic acid, etc. Particularly suitable salts include sodium tetraborate and ammonium pentaborate. Such electrolytes typically have an electrical conductivity of from about 0.1 to about 20 mS/cm, in some embodiments from about 0.5 to about 10 mS/cm, and in some embodiments, from about 1 to about 5 mS/cm, determined at a temperature of 25° C.

If desired, each stage of anodization may be repeated for one or more cycles to achieve the desired dielectric thickness. Furthermore, the anode body may also be rinsed or washed with another solvent (e.g., water) after the first and/or second stages to remove the electrolyte.

C. Solid Electrolyte

A solid electrolyte overlies the dielectric that generally functions as the cathode for the capacitor. In one embodiment, the cathode of the solid electrolytic capacitor can be made principally from manganese dioxide and can be formed by a process generically termed manganizing. In this process, a conductive counter electrode coating is formed over the dielectric formed from anodizing. The manganizing step is typically performed by dipping the anodized device in a solution of manganous nitrate and heating the impregnated device in a moist atmosphere to convert the nitrate to a solid conductive manganese dioxide. In other words, a manganese dioxide solid electrolyte may be formed by the pyrolytic decomposition of manganous nitrate ($Mn(NO_3)_2$).

In another embodiment, the solid electrolyte may also be formed from one or more conductive polymer layers. For instance, the solid electrolyte can contain a conductive polymer, which is typically π-conjugated and have electrical conductivity after oxidation or reduction, such as an electrical conductivity of at least about 1 μS/cm. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. Suitable polythiophenes may include, for instance, polythiophene and derivatives thereof, such as poly(3,4-ethylenedioxythiophene) ("PEDT"). In one particular embodiment, a polythiophene derivative is employed with recurring units of general formula (I) or formula (II) or recurring units of general formulae (I) and (II):

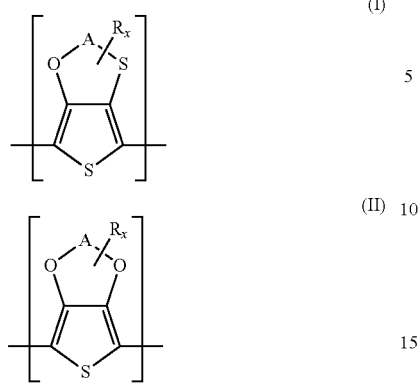

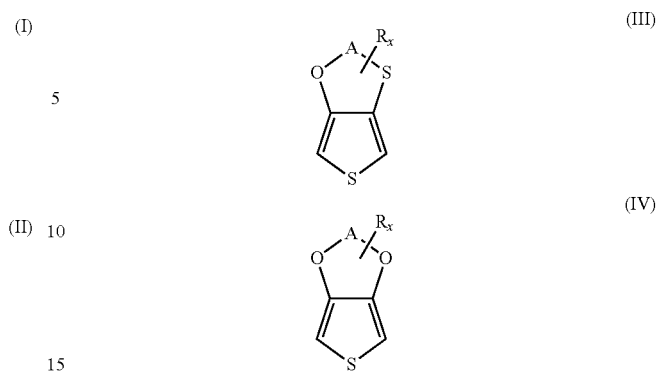

wherein, A, R, and X are as defined above.

wherein,

A is an optionally substituted $C_1$ to $C_5$ alkylene radical (e.g., methylene, ethylene, n-propylene, n-butylene, n-pentylene, etc.);

R is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and x is an integer from 0 to 8, in some embodiments, from 0 to 2, and in some embodiments, x is 0. Example of substituents for the radicals "A" or "R" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

The total number of recurring units of general formula (I) or formula (II) or of general formulae (I) and (II) is typically from 2 to 2,000, and in some embodiments, from 2 to 100.

Particularly suitable polythiophene derivatives are those in which "A" is an optionally substituted $C_2$ to $C_3$ alkylene radical and x is 0 or 1. In one particular embodiment, the polythiophene derivative is PEDT and has recurring units of formula (II), wherein "A" is $CH_2$—$CH_2$ and "x" is 0. Methods for forming such polythiophene derivatives are well known in the art and described, for instance, in U.S. Pat. No. 6,987,663 to Merker, et al., which is incorporated herein in its entirety by reference thereto for all purposes. For example, the polythiophene derivatives may be formed from a monomeric precursor, such as optionally substituted thiophenes. Particularly suitable monomeric precursors are substituted 3,4-alkylenedioxythiophenes having the general formula (III), (IV) or a mixture of thiophene of general formulae (III) and (IV):

Examples of such monomeric precursors include, for instance, optionally substituted 3,4-ethylenedioxythiophenes. Derivatives of these monomeric precursors may also be employed that are, for example, dimers or trimers of the above monomeric precursors. Higher molecular derivatives, i.e., tetramers, pentamers, etc. of the monomeric precursors are suitable for use in the present invention. The derivatives may be made up of identical or different monomer units and used in pure form and in a mixture with one another and/or with the monomeric precursors. Oxidized or reduced forms of these precursors may also be employed.

To produce the desired conductive polymer, monomeric precursors, such as described above, typically undergo oxidative polymerization in the presence of an oxidizing agent. The oxidizing agent may be a transition metal salt, such as a salt of an inorganic or organic acid that contain iron(III), copper(II), chromium(VI), cerium(IV), manganese(IV), manganese(VII), or ruthenium(III) cations. Particularly suitable transition metal salts include iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable for use in the present invention.

Various methods may be utilized to apply the solid electrolyte onto the anode part. In one embodiment, the oxidizing agent and monomeric precursor are applied, either sequentially or together, such that the polymerization reaction occurs in situ on the part. Suitable application techniques may include screen-printing, dipping, electrophoretic coating, and spraying, may be used to form a conductive polymer coating. As an example, the monomeric precursor (e.g., 3,4-ethylenedioxy-thiophene) may initially be mixed with the oxidizing agent to form a solution. One suitable oxidizing agent is CLEVIOS™ C, which is iron III toluenesulfonate and sold by Heraeus. CLEVIOS™ C is a commercially available catalyst for CLEVIOS™ M, which is 3,4-ethylene dioxythiophene, a PEDT monomer also sold by Heraeus. Once the mixture is formed, the anode part may then be dipped into the solution so that the polymer forms on the surface of the anode part. Alternatively, the oxidizing agent and precursor may also be applied separately to the anode part. In one embodiment, for example, the oxidizing agent is dissolved in an organic solvent (e.g., butanol) and then applied to the anode part as a dipping solution. The anode part may then be dried to remove the solvent therefrom. Thereafter, the anode part may be dipped into a solution containing the appropriate monomer.

As the monomer contacts the surface of the anode part containing the oxidizing agent, it may chemically polymerize thereon. Polymerization may be performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Publication No. 2008/232037 to Biler. Still other methods for applying such conductive polymer coating(s) may be described in U.S. Pat. No. 5,457,862 to Sakata, et al., U.S. Pat. No. 5,473,503 to Sakata, et al., U.S. Pat. No. 5,729,428 to Sakata, et al., and U.S. Pat. No. 5,812,367 to Kudoh, et al., which are incorporated herein in their entirety by reference thereto for all purposes.

In addition to in situ application, the solid electrolyte may also be applied to the part in the form of a dispersion of solid conductive polymer particles. Although their size may vary, it is typically desired that the particles possess a small diameter to increase the surface area available for adhering to the anode part. To enable good impregnation of the anode body, the particles employed in the dispersion typically have a small size, such as an average size (e.g., diameter) of from about 1 to about 150 nanometers, in some embodiments from about 2 to about 50 nanometers, and in some embodiments, from about 5 to about 40 nanometers. The diameter of the particles may be determined using known techniques, such as by ultracentrifuge, laser diffraction, etc. The shape of the particles may likewise vary. In one particular embodiment, for instance, the particles are spherical in shape. However, it should be understood that other shapes are also contemplated by the present invention, such as plates, rods, discs, bars, tubes, irregular shapes, etc. The concentration of the particles in the dispersion may vary depending on the desired viscosity of the dispersion and the particular manner in which the dispersion is to be applied to the capacitor. Typically, however, the particles constitute from about 0.1 to about 10 wt. %, in some embodiments from about 0.4 to about 5 wt. %, and in some embodiments, from about 0.5 to about 4 wt. % of the dispersion.

The formation of the conductive polymers into a particulate form may be enhanced by using a separate counterion to counteract a charged conductive polymer (e.g., polythiophene). That is, the conductive polymer (e.g., polythiophene or derivative thereof) used in the solid electrolyte typically has a charge on the main polymer chain that is neutral or positive (cationic). Polythiophene derivatives, for instance, typically carry a positive charge in the main polymer chain.

In some cases, the polymer may possess positive and negative charges in the structural unit, with the positive charge being located on the main chain and the negative charge optionally on the substituents of the radical "R", such as sulfonate or carboxylate groups. The positive charges of the main chain may be partially or wholly saturated with the optionally present anionic groups on the radicals "R." Viewed overall, the polythiophenes may, in these cases, be cationic, neutral or even anionic. Nevertheless, they are all regarded as cationic polythiophenes as the polythiophene main chain has a positive charge.

The counterion may be a monomeric or polymeric anion. Polymeric anions can, for example, be anions of polymeric carboxylic acids (e.g., polyacrylic acids, polymethacrylic acid, polymaleic acids, etc.); polymeric sulfonic acids (e.g., polystyrene sulfonic acids ("PSS"), polyvinyl sulfonic acids, etc.); and so forth. The acids may also be copolymers, such as copolymers of vinyl carboxylic and vinyl sulfonic acids with other polymerizable monomers, such as acrylic acid esters and styrene. Likewise, suitable monomeric anions include, for example, anions of $C_1$ to $C_{20}$ alkane sulfonic acids (e.g., dodecane sulfonic acid); aliphatic perfluorosulfonic acids (e.g., trifluoromethane sulfonic acid, perfluorobutane sulfonic acid or perfluorooctane sulfonic acid); aliphatic $C_1$ to $C_{20}$ carboxylic acids (e.g., 2-ethyl-hexylcarboxylic acid); aliphatic perfluorocarboxylic acids (e.g., trifluoroacetic acid or perfluorooctanoic acid); aromatic sulfonic acids optionally substituted by $C_1$ to $C_{20}$ alkyl groups (e.g., benzene sulfonic acid, o-toluene sulfonic acid, p-toluene sulfonic acid or dodecylbenzene sulfonic acid); cycloalkane sulfonic acids (e.g., camphor sulfonic acid or tetrafluoroborates, hexafluorophosphates, perchlorates, hexafluoroantimonates, hexafluoroarsenates or hexachloroantimonates); and so forth. Particularly suitable counteranions are polymeric anions, such as a polymeric carboxylic or sulfonic acid (e.g., polystyrene sulfonic acid ("PSS")). The molecular weight of such polymeric anions typically ranges from about 1,000 to about 2,000,000, and in some embodiments, from about 2,000 to about 500,000.

When employed, the weight ratio of such counterions to conductive polymers in a given layer of the solid electrolyte is typically from about 0.5:1 to about 50:1, in some embodiments from about 1:1 to about 30:1, and in some embodiments, from about 2:1 to about 20:1. The weight of the electrically conductive polymers corresponds referred to the above-referenced weight ratios refers to the weighed-in portion of the monomers used, assuming that a complete conversion occurs during polymerization.

In addition to conductive polymer(s) and optional counterion(s), the dispersion may also contain one or more binders to further enhance the adhesive nature of the polymeric layer and also increase the stability of the particles within the dispersion. The binders may be organic in nature, such as polyvinyl alcohols, polyvinyl pyrrolidones, polyvinyl chlorides, polyvinyl acetates, polyvinyl butyrates, polyacrylic acid esters, polyacrylic acid amides, polymethacrylic acid esters, polymethacrylic acid amides, polyacrylonitriles, styrene/acrylic acid ester, vinyl acetate/acrylic acid ester and ethylene/vinyl acetate copolymers, polybutadienes, polyisoprenes, polystyrenes, polyethers, polyesters, polycarbonates, polyurethanes, polyamides, polyimides, polysulfones, melamine formaldehyde resins, epoxide resins, silicone resins or celluloses. Crosslinking agents may also be employed to enhance the adhesion capacity of the binders. Such crosslinking agents may include, for instance, melamine compounds, masked isocyanates or functional silanes, such as 3-glycidoxypropyltrialkoxysilane, tetraethoxysilane and tetraethoxysilane hydrolysate or crosslinkable polymers, such as polyurethanes, polyacrylates or polyolefins, and subsequent crosslinking.

Dispersion agents may also be employed to facilitate the formation of the solid electrolyte and the ability to apply it to the anode part. Suitable dispersion agents include solvents, such as aliphatic alcohols (e.g., methanol, ethanol, i-propanol and butanol), aliphatic ketones (e.g., acetone and methyl ethyl ketones), aliphatic carboxylic acid esters (e.g., ethyl acetate and butyl acetate), aromatic hydrocarbons (e.g., toluene and xylene), aliphatic hydrocarbons (e.g., hexane, heptane and cyclohexane), chlorinated hydrocarbons (e.g., dichloromethane and dichloroethane), aliphatic nitriles (e.g., acetonitrile), aliphatic sulfoxides and sulfones (e.g., dimethyl sulfoxide and sulfolane), aliphatic carboxylic acid amides (e.g., methylacetamide, dimethylacetamide and dimethylformamide), aliphatic and araliphatic ethers (e.g., diethylether and anisole), water, and mixtures of any of the foregoing solvents. A particularly suitable dispersion agent is water.

In addition to those mentioned above, still other ingredients may also be used in the dispersion. For example, conventional fillers may be used that have a size of from about 10 nanometers to about 100 micrometers, in some embodiments from about 50 nanometers to about 50 micrometers, and in some embodiments, from about 100 nanometers to about 30 micrometers. Examples of such fillers include calcium carbonate, silicates, silica, calcium or barium sulfate, aluminum hydroxide, glass fibers or bulbs, wood flour, cellulose powder carbon black, electrically conductive polymers, etc. The fillers may be introduced into the dispersion in powder form, but may also be present in another form, such as fibers.

Surface-active substances may also be employed in the dispersion, such as ionic or non-ionic surfactants. Furthermore, adhesives may be employed, such as organofunctional silanes or their hydrolysates, for example 3-glycidoxypropyltrialkoxysilane, 3-aminopropyl-triethoxysilane, 3-mercaptopropyl-trimethoxysilane, 3-metacryloxypropylt-rimethoxysilane, vinyltrimethoxysilane or octyltriethoxysilane. The dispersion may also contain additives that increase conductivity, such as ether group-containing compounds (e.g., tetrahydrofuran), lactone group-containing compounds (e.g., γ-butyrolactone or γ-valerolactone), amide or lactam group-containing compounds (e.g., caprolactam, N-methylcaprolactam, N,N-dimethylacetamide, N-methylacetamide, N,N-dimethylformamide (DMF), N-methylformamide, N-methylformanilide, N-methylpyrrolidone (NMP), N-octylpyrrolidone, or pyrrolidone), sulfones and sulfoxides (e.g., sulfolane (tetramethylenesulfone) or dimethylsulfoxide (DMSO)), sugar or sugar derivatives (e.g., saccharose, glucose, fructose, or lactose), sugar alcohols (e.g., sorbitol or mannitol), furan derivatives (e.g., 2-furancarboxylic acid or 3-furancarboxylic acid), and alcohols (e.g., ethylene glycol, glycerol, di- or triethylene glycol).

The polymeric dispersion may be applied to the part using a variety of known techniques, such as by spin coating, impregnation, pouring, dropwise application, injection, spraying, doctor blading, brushing or printing (e.g., ink-jet, screen, or pad printing). Although it may vary depending on the application technique employed, the viscosity of the dispersion is typically from about 0.1 to about 100,000 mPa·s (measured at a shear rate of 100 s$^{-1}$), in some embodiments from about 1 to about 10,000 mPa·s, in some embodiments from about 10 to about 1,500 mPa·s, and in some embodiments, from about 100 to about 1000 mPa·s.

Once applied, the layer may be dried and washed. One or more additional layers may also be formed in this manner to achieve the desired thickness. Typically, the total thickness of the layer(s) formed by this particle dispersion is from about 1 to about 50 µm, and in some embodiments, from about 5 to about 20 µm. The weight ratio of counterions to conductive polymers is likewise from about 0.5:1 to about 50:1, in some embodiments from about 1:1 to about 30:1, and in some embodiments, from about 2:1 to about 20:1.

In addition to applying the solid electrolyte via in situ polymerization or via the application of a dispersion of conductive polymer particles, it is also to be understood that the solid electrolyte can be applied via a hybrid process that combines both in situ polymerization and the application of a dispersion of conductive polymer particles. For example, in one embodiment, a capacitor element can include a solid electrolyte formed from multiple layers. More specifically, the solid electrolyte can include a first conductive polymer layer that is in contact with a dielectric that overlies an anode body. The first layer may contain a conductive polymer (e.g., PEDT) that is formed through in situ polymerization of an oxidizing agent and monomeric precursor. The solid electrolyte can also contain a second conductive polymer layer that generally overlies the first layer. The second layer may be formed from a dispersion of particles that contains a conductive polymer (e.g., PEDT), binder, and an optional counterion (e.g., PSS). One benefit of employing such a dispersion is that it may be able to penetrate into the edge region of the capacitor body to achieve good electrical contact with the inner layer and increase the adhesion to the capacitor body. This results in a more mechanically robust part, which may reduce equivalent series resistance and leakage current. On the other hand, in another embodiment, the solid electrolyte may be a single conductive polymer layer. Regardless of how many layers it includes, the resulting solid electrolyte typically has a total thickness of from about 1 micrometer (µm) to about 200 µm, in some embodiments from about 2 µm to about 50 µm, and in some embodiments, from about 5 µm to about 30 µm. Further, if the solid electrolyte includes two layers such as an inner layer and an outer layer, the inner layer may have a total thickness of from about 0.1 µm to about 100 µm, in some embodiments from about 0.5 µm to about 20 µm, and in some embodiments, from about 1 µm to about 5 µm, while the outer layer may have a total thickness of from about 0.2 µm to about 100 µm, in some embodiments from about 1 µm to about 40 µm, and in some embodiments, from about 3 µm to about 10 µm.

Regardless of the particular manner in which it is formed, the solid electrolyte may be healed upon application to the anode part. Healing may occur after each application of a solid electrolyte layer or may occur after the application of the entire coating if multiple layers are employed. In some embodiments, for example, the solid electrolyte may be healed by dipping the pellet into an electrolyte solution, such as a solution of acid, and thereafter applying a constant voltage to the solution until the current is reduced to a preselected level. If desired, such healing may be accomplished in multiple steps. After application of some or all of the layers described above, the resulting part may then be washed if desired to remove various byproducts, excess oxidizing agents, and so forth. Further, in some instances, drying may be utilized after some or all of the dipping operations described above. For example, drying may be desired after applying the oxidizing agent and/or after washing the pellet in order to open the pores of the part so that it can receive a liquid during subsequent dipping steps.

D. Additional Layers

If desired, the capacitor may also contain other layers as is known in the art. For example, a protective coating may optionally be formed between the dielectric and solid electrolyte, such as one made of a relatively insulative resinous material (natural or synthetic). Such materials may have a specific resistivity of greater than about 10 W/cm, in some embodiments greater than about 100, in some embodiments greater than about 1,000 W/cm, in some embodiments greater than about 1×105 W/cm, and in some embodiments, greater than about 1×1010 W/cm. Some resinous materials that may be utilized in the present invention include, but are not limited to, polyurethane, polystyrene, esters of unsaturated or saturated fatty acids (e.g., glycerides), and so forth. For instance, suitable esters of fatty acids include, but are not limited to, esters of lauric acid, myristic acid, palmitic acid, stearic acid, eleostearic acid, oleic acid, linoleic acid, linolenic acid, aleuritic acid, shellolic acid, and so forth. These esters of fatty acids have been found particularly useful when used in relatively complex combinations to form a "drying oil", which allows the resulting film to rapidly polymerize into a stable layer. Such drying oils may include mono-, di-, and/or tri-glycerides, which have a glycerol backbone with one, two, and three, respectively, fatty acyl residues that are esterified. For instance, some suitable drying oils that may be used include, but are not limited to, olive oil, linseed oil, castor oil, tung oil, soybean oil, and shellac. These and other protective coating materials are described in more detail U.S. Pat. No. 6,674,635 to Fife, et al., which is incorporated herein in its entirety by reference thereto for all purposes.

The anode part may also be applied with a carbon layer (e.g., graphite) and silver layer, respectively. The silver coating may, for instance, act as a solderable conductor, contact layer, and/or charge collector for the capacitor and the carbon coating may limit contact of the silver coating with the solid electrolyte. Such coatings may cover some or all of the solid electrolyte.

E. Terminations

The capacitor may also be provided with terminations, particularly when employed in surface mounting applications. For example, the capacitor may contain an anode termination to which the anode of the capacitor element is electrically connected and a cathode termination to which the cathode of the capacitor element is electrically connected. Any conductive material may be employed to form the terminations, such as a conductive metal (e.g., copper, nickel, silver, nickel, zinc, tin, palladium, lead, copper, aluminum, molybdenum, titanium, iron, zirconium, magnesium, and alloys thereof). Particularly suitable conductive metals include, for instance, copper, copper alloys (e.g., copper-zirconium, copper-magnesium, copper-zinc, or copper-iron), nickel, and nickel alloys (e.g., nickel-iron). The thickness of the terminations is generally selected to minimize the thickness of the capacitor. For instance, the thickness of the terminations may range from about 0.05 to about 1 millimeter, in some embodiments from about 0.05 to about 0.5 millimeters, and from about 0.07 to about 0.2 millimeters. One exemplary conductive material is a copper-iron alloy metal plate available from Wieland (Germany). If desired, the surface of the terminations may be electroplated with nickel, silver, gold, tin, etc. as is known in the art to ensure that the final part is mountable to the circuit board. In one particular embodiment, both surfaces of the terminations are plated with nickel and silver flashes, respectively, while the mounting surface is also plated with a tin solder layer.

Figure 12:
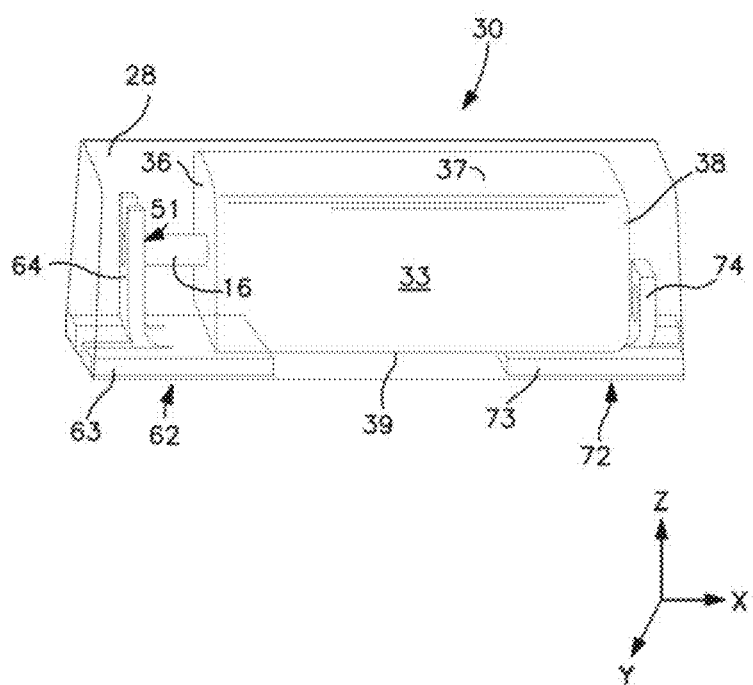
FIG. 12 is a schematic illustration of one embodiment of a solid electrolytic capacitor that may be formed in accordance with the present invention.

Referring to FIG. 12, for example, an electrolytic capacitor 30 is shown as including an anode termination 62 and a cathode termination 72 in electrical connection with the capacitor element 33, where the capacitor element 33 includes the porous anode body, dielectric, and solid electrolyte components discussed above. The capacitor element 33 has an upper surface 37, lower surface 39, front surface 36, and rear surface 38. Although it may be in electrical contact with any of the surfaces of the capacitor element 33, the cathode termination 72 in the illustrated embodiment is in electrical contact with the lower surface 39 via a conductive adhesive (not shown). More specifically, the cathode termination 72 contains a first component 73 that is in electrical contact and generally parallel with the lower surface 39 of the capacitor element 33. The anode termination 62 likewise contains a first component 63 positioned substantially perpendicular to a second component 64. The first component 63 is in electrical contact and generally parallel with the lower surface 39 of the capacitor element 33. The second component 64 contains a region 51 that carries an anode lead 16. The region 51 may possess a "U-shape" to further enhance surface contact and mechanical stability of the lead 16.

The terminations may be connected to the capacitor element using any technique known in the art. In one embodiment, for example, a lead frame may be provided that defines the cathode termination 72 and anode termination 62. To attach the electrolytic capacitor element 33 to the lead frame, the conductive adhesive (not shown) may initially be applied to a surface of the cathode termination 72. The conductive adhesive may include, for instance, conductive metal particles contained with a resin composition. The metal particles may be silver, copper, gold, platinum, nickel, zinc, bismuth, etc. The resin composition may include a thermoset resin (e.g., epoxy resin), curing agent (e.g., acid anhydride), and coupling agent (e.g., silane coupling agents). Suitable conductive adhesives may be described in U.S. Patent Publication No. 2006/0038304 to Osako, et al. Any of a variety of techniques may be used to apply the conductive adhesive to the cathode termination 72. Printing techniques, for instance, may be employed due to their practical and cost-saving benefits.

A variety of methods may generally be employed to attach the terminations to the capacitor. In one embodiment, for example, the second component 64 of the anode termination 62 is initially bent upward to the position shown in FIG. 12. Thereafter, the capacitor element 33 is positioned on the cathode termination 72 so that its lower surface 39 contacts the adhesive 90 and the anode lead 16 is received by the region 51. If desired, an insulating material (not shown), such as a plastic pad or tape, may be positioned between the lower surface 39 of the capacitor element 33 and the first component 63 of the anode termination 62 to electrically isolate the anode and cathode terminations.

The anode lead 16 is then electrically connected to the region 51 using any technique known in the art, such as mechanical welding, laser welding, conductive adhesives, etc. For example, the anode lead 16 may be welded to the anode termination 62 using a laser. Lasers generally contain resonators that include a laser medium capable of releasing photons by stimulated emission and an energy source that excites the elements of the laser medium. One type of suitable laser is one in which the laser medium consist of an aluminum and yttrium garnet (YAG), doped with neodymium (Nd). The excited particles are neodymium ions $Nd^{3+}$. The energy source may provide continuous energy to the laser medium to emit a continuous laser beam or energy discharges to emit a pulsed laser beam. Upon electrically connecting the anode lead 16 to the anode termination 62, the conductive adhesive may then be cured. For example, a heat press may be used to apply heat and pressure to ensure that the electrolytic capacitor element 33 is adequately adhered to the cathode termination 72 by the adhesive.

F. Casing

The capacitor element is generally encapsulated within a casing so that at least a portion of the anode and cathode terminations are exposed for mounting onto a circuit board. As shown in FIG. 12, for instance, the capacitor element 33 is encapsulated within a resinous casing 28 so that a portion of the anode termination 62 and a portion of the cathode termination 72 are exposed. The casing is typically formed from a thermoset resin. Examples of such resins include, for instance, epoxy resins, polyimide resins, melamine resins, urea-formaldehyde resins, polyurethane resins, phenolic resins, polyester resins, etc. Epoxy resins are also particularly suitable. Still other additives may also be employed, such as photoinitiators, viscosity modifiers, suspension aiding agents, pigments, stress reducing agents, non-conductive fillers, stabilizers, etc. For example, the non-conductive fillers may include inorganic oxide particles, such as silica, alumina, zirconia, magnesium oxide, iron oxide, copper oxide, zeolites, silicates, clays (e.g., smectite clay), etc., as well as composites (e.g., alumina-coated silica particles) and mixtures thereof.

IV. Wet Electrolytic Capacitor Containing a Valve Metal Sourced from a Conflict-Free Mine Site It should also be understood that although the capacitor and the method of forming thereof discussed above references a solid electrolytic capacitor specifically, the present invention also contemplates any other type of electrolytic capacitor that includes a valve metal, such as a wet electrolytic capacitor. The wet electrolytic capacitor contemplated by the present invention can include an anode formed from an anodically oxidized sintered porous pellet, a cathode, and a fluidic working electrolyte. The pellet may be formed from a pressed valve metal powder, and the pellet can be anodically oxidized so that a dielectric layer is formed over and/or within the anode, as generally described above with respect to the solid electrolytic capacitor of the present invention. The wet electrolytic capacitor also includes a working electrolyte that is electrical communication with the anode and cathode. The electrolyte is a fluid that may be impregnated within the anode, or it may be added to the capacitor at a later stage of production. The fluid electrolyte generally uniformly wets the dielectric on the anode. Various suitable electrolytes are described in U.S. Pat. Nos. 5,369,547 and 6,594,140 to Evans, et al. Typically, the electrolyte is ionically conductive in that has an electrical conductivity of from about 0.1 to about 20 Siemens per centimeter ("S/cm"), in some embodiments from about 0.2 to about 15 S/cm, and in some embodiments, from about 0.5 to about 10 S/cm, determined at a temperature of about 23° C. using any known electric conductivity meter (e.g., Oakton Con Series 11). The fluid electrolyte is generally in the form of a liquid, such as a solution (e.g., aqueous or non-aqueous), colloidal suspension, gel, etc. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution). Various other electrolytes are described in U.S. Pat. Nos. 5,369,547 and 6,594,140 to Evans, et al.

Further, the cathode of the wet electrolytic capacitor typically contains a metal substrate, which may also optionally serve as a casing for the capacitor. The substrate may be formed from a variety of different metals, such as tantalum, niobium, aluminum, nickel, hafnium, titanium, copper, silver, steel (e.g., stainless), alloys thereof, composites thereof (e.g., metal coated with electrically conductive oxide), and so forth. The geometric configuration of the substrate may generally vary as is well known to those skilled in the art, such as in the form of a foil, sheet, screen, container, can, etc. The metal substrate may form the all or a portion of casing for the capacitor, or it may simply be applied to the casing. Regardless, the substrate may have a variety of shapes, such as generally cylindrical, D-shaped, rectangular, triangular, prismatic, etc. If desired, a surface of the substrate may be roughened to increase its surface area and increase the degree to which a material may be able to adhere thereto. In one embodiment, for example, a surface of the substrate is chemically etched, such as by applying a solution of a corrosive substance (e.g., hydrochloric acid) to the surface. Mechanical roughening may also be employed. For instance, a surface of the substrate may be abrasive blasted by propelling a stream of abrasive media (e.g., sand) against at least a portion of a surface thereof.

A conductive coating may also be disposed on a surface of the metal substrate (e.g., interior surface) to serve as an electrochemically active material for the capacitor. Any number of layers may be employed in the coating. The materials employed in the coating may vary. For example, the conductive coating may contain a noble metal (e.g., ruthenium, rhodium, palladium, silver, osmium, iridium, platinum, gold, etc.), an oxide (e.g., ruthenium oxide), carbonaceous materials, conductive polymers, etc. In one embodiment, for example, the coating may include conductive polymer(s) that are typically π-conjugated and have electrical conductivity after oxidation or reduction. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. Substituted polythiophenes are particularly suitable for use as conductive polymer in that they have particularly good mechanical robustness and electrical performance.

Figure 13:
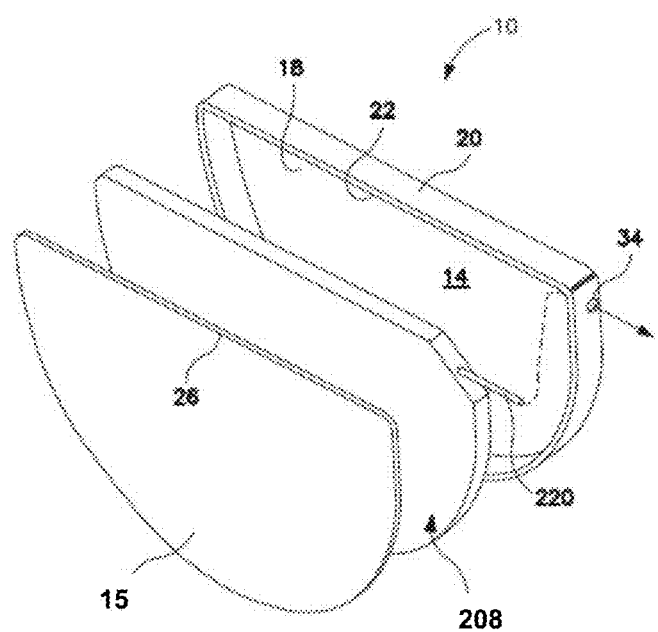
FIG. 13 is an exploded schematic illustration of a wet electrolytic capacitor that may be formed in accordance with the present invention.

As shown in FIG. 13, the anode 208 of the wet electrolytic capacitor 10 may be positioned within a casing 12 made of a first casing member 14 and a second casing member 15. The first casing member 14 can have a face wall 18 joined to a surrounding sidewall 20, which extends to an edge 22. The second casing member 15 may likewise contain a second face wall 24 having a surrounding edge 26. In the illustrated embodiment, the second casing member 15 is thus in the form of a plate that serves as a lid for the casing 10. The casing members 14 and 15 may be hermetically sealed together by welding (e.g., laser welding) the edges 22 and 26 where they contact each other. The casing members 14 and/or 15 may be analogous to the metal substrate described above such that a conductive polymer coating (not shown) may be deposited on the interior surface thereof. Alternatively, a separate metal substrate may be located adjacent to the casing member 14 and/or 16 and applied with the conductive polymer coating.

Although not shown, one or more separators may be employed between the anode and cathode (e.g., between the anode 208 and the first casing member 14, between the anode 208 and the second casing member 15, or between the anode 208 and both casing members 14 and 15) that help insulate the anode 208 and conductive polymer-coated cathode from each other. Examples of suitable materials for this purpose include, for instance, porous polymer materials (e.g., polypropylene, polyethylene, etc.), porous inorganic materials (e.g., fiberglass mats, porous glass paper, etc.), ion exchange resin materials, etc. Particular examples include ionic perfluoronated sulfonic acid polymer membranes (e.g., Nafion™ from the E.I. DuPont de Nemeours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes.

A feedthrough may also be employed that electrically insulates the anode wire 220 from the casing 12. The feedthrough can extend from within the casing 12 to the outside thereof, where a hole 34 may be provided in the surrounding sidewall 20 of the casing member 14. The feedthrough may, for example, be a glass-to-metal seal ("GTMS") that contains a ferrule with an internal cylindrical bore of a constant inside diameter. An insulative glass can thus provide a hermetic seal between the bore and the anode wire 220 passing therethrough. After assembly and sealing (e.g., welding), the electrolyte may optionally be introduced into the casing through a fill-port. Filling may be accomplished by placing the capacitor in a vacuum chamber so that the fill-port extends into a reservoir of the electrolyte. When the chamber is evacuated, pressure is reduced inside the capacitor. When the vacuum is released, pressure inside the capacitor re-equilibrates, and the electrolyte is drawn through the fill-port into the capacitor.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method of forming an electrolytic capacitor, the method comprising:
    obtaining an unverified mineral sample from a mine site;
    analyzing the unverified mineral sample via quantitative mineralogical analysis and comparing data collected during the quantitative mineralogical analysis for the unverified mineral sample to data in a database that corresponds to quantitative mineralogical analysis collected for verified mineral samples sourced from one or more mine sites from a conflict-free geographic region to determine if the unverified mineral sample is sourced from the one or more mine sites from the conflict-free geographic region, wherein analyzing the unverified mineral sample via quantitative mineralogical analysis comprises performing automated mineralogy testing on the unverified mineral sample and identifying grains for additional testing based on data obtained during automated mineralogy testing, wherein from about 25 grains to about 125 grains are identified for additional testing; and
    if it is determined that the unverified mineral sample is sourced from the one or more mine sites from the conflict-free geographic region, converting the unverified mineral sample into an anode for the electrolytic capacitor.

2. The method of claim 1, further comprising rejecting the unverified mineral sample if it cannot be determined that the mineral sample is sourced from the one or more mine sites from the conflict-free geographic region.

3. The method of claim 1, wherein the conflict-free geographic region excludes the Democratic Republic of Congo, Angola, Burundi, Central African Republic, Congo Republic, Rwanda, Sudan, Tanzania, Uganda, and Zambia.

4. The method of 1, further comprising performing one or more chemical assays on the unverified mineral sample, wherein the one or more chemical assays determines the amount of uranium, thorium, or tantalum present in the unverified mineral sample.

5. The method of claim 1, wherein analyzing the unverified mineral sample via quantitative mineralogical analysis comprises polishing the unverified mineral sample to expose grain interiors present in the unverified mineral sample.

6. The method of claim 1, further comprising performing electron micro probe analysis (EMPA) on the identified grains.

7. The method of claim 6, further comprising performing laser ablation inductively coupled plasma spectrometry (LA-ICP-MS) on the identified grains.

8. The method of claim 7, wherein it is determined that the unverified mineral sample is sourced from the one or mine sites from the conflict-free geographic region if data collected during the automated mineralogy testing, LA-ICP-MS, and/or EMPA for the unverified mineral sample substantially matches data collected during the automated mineralogy testing, LA-ICP-MS, and/or EMPA for one of the verified mineral samples sourced from the one or mine sites from the conflict-free geographic region.

9. The method of claim 1, wherein the unverified mineral sample comprises a valve metal, wherein the valve metal comprises tantalum, niobium, or a combination thereof.

10. The method of claim 9, wherein converting the unverified mineral sample into the anode for the electrolytic capacitor comprises:
    separating the valve metal from the unverified mineral sample;
    forming the valve metal into a valve metal powder;
    pressing the valve metal powder to form the anode; and
    sintering the anode.

11. The method of claim 10, further comprising forming a dielectric layer over the sintered anode.

12. The method of claim 1, wherein the electrolytic capacitor is a solid electrolytic capacitor.

13. The method of claim 12, wherein the solid electrolytic capacitor includes a solid electrolyte.

14. The method of claim 13, wherein solid electrolyte includes a conductive polymer or manganese dioxide.

15. The method of claim 1, wherein the electrolytic capacitor is a wet electrolytic capacitor.

16. The method of claim 15, wherein the wet electrolytic capacitor includes a cathode comprising a metal substrate coated with a conductive coating and a fluidic working electrolyte in communication with the anode and the cathode.

17. An electrolytic capacitor formed according to the method of claim 1.

* * * * *